(12) United States Patent
Takahashi et al.

(10) Patent No.: US 12,377,007 B2
(45) Date of Patent: Aug. 5, 2025

(54) GAIT MOTION ASSISTING APPARATUS

(71) Applicants: Suncall Corporation, Kyoto (JP); National University Corporation Kyoto Institute of Technology, Kyoto (JP); Kyoto University, Kyoto (JP)

(72) Inventors: Rei Takahashi, Kyoto (JP); Yukinobu Makihara, Tokyo (JP); Yuichi Sawada, Kyoto (JP); Yoshiyuki Higashi, Kyoto (JP); Koji Ohata, Kyoto (JP)

(73) Assignee: Suncall Corporation, Kyoto (JP)

( * ) Notice: Subject to any disclaimer, the term of this patent is extended or adjusted under 35 U.S.C. 154(b) by 950 days.

(21) Appl. No.: 17/598,789

(22) PCT Filed: Feb. 25, 2020

(86) PCT No.: PCT/JP2020/007312
§ 371 (c)(1),
(2) Date: Sep. 27, 2021

(87) PCT Pub. No.: WO2020/195447
PCT Pub. Date: Oct. 1, 2020

(65) Prior Publication Data
US 2022/0168166 A1 Jun. 2, 2022

(30) Foreign Application Priority Data
Mar. 28, 2019 (JP) .................. 2019-062404

(51) Int. Cl.
*A61H 1/02* (2006.01)
*A61B 5/11* (2006.01)
*A61H 3/00* (2006.01)

(52) U.S. Cl.
CPC ............ *A61H 1/0262* (2013.01); *A61B 5/112* (2013.01); *A61H 3/00* (2013.01);
(Continued)

(58) Field of Classification Search
CPC .... A61H 1/0262; A61H 1/0237; A61H 1/024; A61H 1/0244; A61H 2201/018;
(Continued)

(56) References Cited

U.S. PATENT DOCUMENTS

2015/0190923 A1* 7/2015 Seo .................. A61H 1/0244
602/16
2020/0315899 A1* 10/2020 Takahashi ............... B25J 11/00
2021/0000678 A1* 1/2021 Yasuhara ............... B25J 11/008

FOREIGN PATENT DOCUMENTS

JP   2016214504 A   12/2016
JP      6148766 B1    5/2017
(Continued)

OTHER PUBLICATIONS

English Machine Translation of JP2018050882A provided by Espacenet (Year: 2018).*
(Continued)

*Primary Examiner* — Joseph D. Boecker
*Assistant Examiner* — Brian T Khong
(74) *Attorney, Agent, or Firm* — Sterne, Kessler, Goldstein & Fox P.L.L.C.

(57) ABSTRACT

A gait motion assisting apparatus is provided, in which a thigh phase angle calculating unit has a latest data transmission process to transmit a thigh phase angle φ(k) at sampling timing S(k) (k is an integer of 1 or more) to a gait motion timing calculating unit and store the same as a reference thigh phase angle φc. Also, a stored data transmission process transmits, instead of the thigh phase angle φ(k), a currently stored reference thigh phase angle φc to the gait motion timing calculating unit and performs the stored data transmission process only when conditions are satisfied such that a thigh phase angle at one sampling timing is smaller than the currently stored reference thigh phase angle and an absolute value of a deviation therebetween is equal to or less (Continued)

than a predetermined threshold, and performs the latest data transmission process in other cases.

5 Claims, 15 Drawing Sheets

(52) U.S. Cl.
CPC .. *A61H 2201/018* (2013.01); *A61H 2201/165* (2013.01); *A61H 2201/5025* (2013.01); *A61H 2201/5069* (2013.01); *A61H 2201/5079* (2013.01); *A61H 2201/5084* (2013.01)

(58) Field of Classification Search
CPC .... A61H 2201/5069; A61H 2201/5079; A61H 2201/5084
See application file for complete search history.

(56) References Cited

FOREIGN PATENT DOCUMENTS

| JP | 2018050882 A | * | 4/2018 |
| WO | 2019093000 A1 |   | 5/2019 |

OTHER PUBLICATIONS

International Search Report issued in International Application No. PCT/JP2020/007312, mailed May 19, 2020, 4 pages.

* cited by examiner

GAIT MOTION ASSISTING APPARATUS

FIELD OF THE INVENTION

The present invention relates to a gait motion assisting apparatus.

BACKGROUND ART

As gait assistance or rehabilitation devices for people with leg disability or people with paralysis due to a stroke or the like, gait motion assisting apparatuses including an actuator such as an electric motor for assisting the motion of a leg have been proposed (see Patent Literature 1 described below).

The gait motion assisting apparatus is attachable to and detachable from a knee-ankle-foot orthosis and is configured to impart gait assisting force in a front-back direction to a lower leg frame of the knee-ankle-foot orthosis.

The gait motion assisting apparatus includes a casing detachably attached to the knee-ankle-foot orthosis, the actuator supported by the casing, a drive arm that pushes the lower leg frame of the knee-ankle-foot orthosis back and forth by a rotational force from the actuator, a thigh orientation detecting unit that detects a hip joint angle that is a front-back swing angle of a user's thigh at a sampling timing $S(k)$ (k is an integer of 1 or more), a thigh phase angle calculating unit that calculates a thigh phase angle $\varphi(k)$ at the sampling timing $S(k)$ based on the hip joint angle from the thigh orientation detecting unit,
a gait motion timing calculating unit that calculates a gait motion timing $T(k)$ during a gait cycle corresponding to the sampling timing $S(k)$ based on the thigh phase angle $\varphi(k)$ (that is, a gait motion timing that is defined using a percentage relative to the gait cycle), an assisting torque calculating unit that has an output torque pattern defining a relationship between a gait motion timing $T(k)$ during a gait cycle and a torque value $P(k)$ to be output and applies a gait motion timing $T(k)$ during a gait cycle to the output torque pattern to calculate the torque value $P(k)$ to be output, and an operational control unit that executes operational control on the actuator so as to output the assisting force having the torque value $P(k)$ calculated by the assisting torque calculating unit.

The gait motion assisting apparatus described above in Patent Literature 1 recognizes the gait motion timing during a gait cycle based on the thigh phase angle $\varphi$ instead of the lower leg that is the target part to which gait assisting force is imparted and, compared to the structure for recognizing the gait motion timing based on the motion of the lower leg, is thus effective in providing an advantage to recognize the gait motion timing without requiring a complicated structure; however, there is room for improvement in a following point.

The thigh phase angle calculating unit calculates a thigh phase angle $\varphi$ ($=-\text{Arctan}(\omega/\theta)+\pi$) based on a hip joint angle $\theta$ input from the thigh orientation detecting unit and a hip joint angular velocity $\omega$ obtained by differentiating the hip joint angle $\theta$.

FIG. 10 schematically illustrates a trajectory diagram obtained by plotting the thigh phase angle $\varphi$ (gait state), which is defined by the hip joint angle $\theta$ and the hip joint angular velocity $\omega$, over a gait cycle.

As shown in FIG. 10, the thigh phase angle $\varphi$ defined by the hip joint angle $\theta$ and the hip joint angular velocity $\omega$ varies between 0 and $2\pi$ during a gait cycle.

Specifically, in a case where the hip joint angles $\theta$ in a state where the thigh is positioned in front of and behind the user's body axis line along the vertical direction are referred to as "positive" and "negative", respectively, and the hip joint angular velocities $\omega$ in a state where the thigh is swung forward and backward are referred to as "positive" and "negative", respectively, when the thigh phase angle $\varphi$ is 0 in a state where the hip joint angle $\theta$ is largest in the "negative" direction and the hip joint angular velocity $\omega$ is "zero", the thigh phase angle $\varphi$ changes from 0 to $\pi/2$ during a period (a gait area A1 in FIG. 10) from a state where the thigh is swung backward to the maximum (a state where the hip joint angle $\theta$ is largest in the "negative" direction and the hip joint angular velocity $\omega$ is "zero", the sampling timing $S(1)$ in FIG. 10) to a state where the thigh moves relatively forward in a swing state and matches the user's body axis line (a state where the hip joint angle $\theta$ is "zero" and the hip joint angular velocity $\omega$ is largest in the "positive" direction).

Then, the thigh phase angle $\varphi$ changes from $\pi/2$ to $\pi$ during a period (a gait area A2 in FIG. 10) from a state where the raised thigh in a swing state matches the user's body axis line (a state where the hip joint angle $\theta$ is "zero" and the hip joint angular velocity $\omega$ is largest in the "positive" direction) to a state where the thigh is further swung relatively forward to the maximum (a state where the hip joint angle $\theta$ is largest in the "positive" direction and the hip joint angular velocity $\omega$ is "zero").

Then, the thigh phase angle $\varphi$ changes from the phase angle of $\pi$ to $3\pi/2$ during a period (a gait area A3 in FIG. 10) from a state where the thigh in a swing state is swung forward to the maximum (a state where the hip joint angle $\theta$ is largest in the "positive" direction and the hip joint angular velocity $\omega$ is "zero") to a state where the thigh enters a stance state after being in contact with the ground through the heel contact and the thigh in the stance state is swung relatively backward to match the user's body axis line (a state where the hip joint angle $\theta$ is "zero" and the hip joint angular velocity $\omega$ is largest in the "negative" direction).

Furthermore, the thigh phase angle $\varphi$ changes from $3\pi/2$ to $2\pi$ during a period (a gait area A4 in FIG. 10) from a state where the thigh in the stance state matches the user's body axis line (a state where the hip joint angle $\theta$ is "zero" and the hip joint angular velocity $\omega$ is largest in the "negative" direction) to a state where the thigh is swung relatively backward and is swung backward to the maximum (a state where the hip joint angle is largest in the "negative" direction and the hip joint angular velocity is "zero").

Furthermore, for the user who is capable of performing the normal gait motion, the thigh phase angle $\varphi$ increases at each sampling timing, i.e., with the elapse of time.

However, for users with leg disability or users with paralysis due to a stroke or the like, there may be a situation where a thigh phase angle $\varphi(k+1)$ at one sampling timing $S(k+1)$ is less than the thigh phase angle $\varphi(k)$ at the sampling timing $S(k)$ immediately before the one sampling timing $S(k+1)$, i.e., a thigh reverse swing phenomenon in which the thigh temporarily returns to the side opposite to the direction in which the thigh is supposed to swing during the normal gait motion.

When such a situation occurs, the output of the actuator changes rapidly in the gait motion assisting apparatus described in Patent Literature 1 described above.

PRIOR ART DOCUMENT

Patent Literature

Patent Literature 1: Japanese Patent No. 6148766

SUMMARY OF THE INVENTION

The present invention has been made in consideration of the conventional technology and has an object to provide a gait motion assisting apparatus that is configured to impart gait assisting force corresponding to the cycle gait motion timing recognized based on the thigh phase angle to the lower leg and that is capable of imparting gait assisting force as smoothly as possible even when a thigh reverse swing phenomenon occurs during a gait cycle, i.e., the user's thigh swings in a direction opposite to the direction in which it is supposed to swing during the normal gait motion.

In order to achieve the object, a first aspect of the present invention provides a gait motion assisting apparatus including: an actuator that imparts assisting force to a user's gait motion; a thigh orientation detecting unit that detects an angle-related signal that is related to a hip joint angle, which is a front-back swing angle of the user's thigh, at each sampling timing; a thigh phase angle calculating unit that calculates a thigh phase angle at each sampling timing based on the angle-related signal; a gait motion timing calculating unit that calculates a cycle gait motion timing that is a percentage relative to a gait cycle based on the thigh phase angle from the thigh phase angle calculating unit; an assisting torque calculating unit that has an output torque pattern defining a relationship between the cycle gait motion timing and a torque value to be output and applies the cycle gait motion timing transmitted from the gait motion timing calculating unit to the output torque pattern to calculate the torque value corresponding to the sampling timing; and an operational control unit that executes operational control on the actuator so as to output assisting force having the torque value calculated by the assisting torque calculating unit, wherein the thigh phase angle calculating unit has a latest data transmission process to transmit a thigh phase angle $\varphi(k)$ calculated based on an angle-related signal at a kth (k is an integer of 1 or more) sampling timing S(k) during a gait cycle as the thigh phase angle at the sampling timing S(k) to the gait motion timing calculating unit and store the thigh phase angle $\varphi(k)$ as a reference thigh phase angle $\varphi c$ and a stored data transmission process to transmit, instead of the thigh phase angle $\varphi(k)$ calculated based on the angle-related signal at the kth sampling timing S(k) during the gait cycle, the currently stored reference thigh phase angle $\varphi c$ as the thigh phase angle at the sampling timing S(k) to the gait motion timing calculating unit and continuously store the currently stored reference thigh phase angle $\varphi c$, performs the stored data transmission process only when conditions are satisfied such that one thigh phase angle calculated based on an angle-related signal at one sampling timing is smaller than the currently stored reference thigh phase angle and an absolute value of a deviation therebetween is equal to or less than a predetermined threshold, and performs the latest data transmission process in other cases.

The gait motion assisting apparatus according to the first aspect of the present invention makes it possible to impart gait assisting force as smoothly as possible even when an unintentional thigh reverse swing phenomenon occurs, since the thigh phase angle calculating unit has the latest data transmission process to transmit the thigh phase angle $\varphi(k)$ calculated based on the angle-related signal at the kth sampling timing S(k) during a gait cycle as the thigh phase angle at the sampling timing S(k) to the gait motion timing calculating unit and store the thigh phase angle $\varphi(k)$ as the reference thigh phase angle $\varphi c$ and the stored data transmission process to transmit, instead of the thigh phase angle $\varphi(k)$ calculated based on the angle-related signal at the kth sampling timing S(k) during the gait cycle, the currently stored reference thigh phase angle $\varphi c$ as the thigh phase angle at the sampling timing S(k) to the gait motion timing calculating unit and continuously store the currently stored reference thigh phase angle $\varphi c$, performs the stored data transmission process only when conditions are satisfied such that one thigh phase angle calculated based on an angle-related signal at one sampling timing is smaller than the currently stored reference thigh phase angle and an absolute value of a deviation therebetween is equal to or less than a predetermined threshold, and performs the latest data transmission process in other cases.

In the first aspect, the predetermined threshold is, for example, $1.8\pi$.

In order to achieve the object, a second aspect of the present invention provides a gait motion assisting apparatus including: an actuator that imparts assisting force to a user's gait motion; a thigh orientation detecting unit that detects an angle-related signal that is related to a hip joint angle, which is a front-back swing angle of the user's thigh, at each sampling timing; a thigh phase angle calculating unit that calculates a thigh phase angle at each sampling timing based on the angle-related signal; a gait motion timing calculating unit that calculates a cycle gait motion timing that is a percentage relative to a gait cycle based on the thigh phase angle from the thigh phase angle calculating unit; an assisting torque calculating unit that has an output torque pattern defining a relationship between the cycle gait motion timing and a torque value to be output and applies the cycle gait motion timing transmitted from the gait motion timing calculating unit to the output torque pattern to calculate the torque value corresponding to the sampling timing; and an operational control unit that executes operational control on the actuator so as to output assisting force having the torque value calculated by the assisting torque calculating unit, wherein the gait motion timing calculating unit has a latest data transmission process to transmit a cycle gait motion timing T(k) calculated based on an angle-related signal at a kth sampling timing S(k) (k is an integer of 1 or more) during a gait cycle as the cycle gait motion timing at the sampling timing S(k) to the assisting torque calculating unit and store the cycle gait motion timing T(k) as a reference cycle gait motion timing Tc and a stored data transmission process to transmit, instead of the cycle gait motion timing T(k) calculated based on the angle-related signal at the kth sampling timing S(k) during the gait cycle, the currently stored reference cycle gait motion timing Tc as the cycle gait motion timing at the sampling timing S(k) to the assisting torque calculating unit and continuously store the currently stored reference cycle gait motion timing Tc, performs the stored data transmission process only when conditions are satisfied such that one cycle gait motion timing calculated based on an angle-related signal at one sampling timing is smaller than the currently stored reference cycle gait motion timing and an absolute value of a deviation therebetween is equal to or less than a predetermined threshold, and performs the latest data transmission process in other cases.

The gait motion assisting apparatus according to the second aspect of the present invention makes it possible to impart gait assisting force as smoothly as possible even when an unintentional thigh reverse swing phenomenon occurs, since the gait motion timing calculating unit has the latest data transmission process to transmit the cycle gait motion timing T(k) calculated based on the angle-related signal at the kth sampling timing S(k) during a gait cycle as the cycle gait motion timing at the sampling timing S(k) to the assisting torque calculating unit and store the cycle gait motion timing T(k) as the reference cycle gait motion timing Tc and the stored data transmission process to transmit, instead of the cycle gait motion timing T(k) calculated based on the angle-related signal at the kth sampling timing S(k) during the gait cycle, the currently stored reference cycle gait motion timing Tc as the cycle gait motion timing at the sampling timing S(k) to the assisting torque calculating unit and continuously store the currently stored reference cycle gait motion timing Tc, performs the stored data transmission process only when conditions are satisfied such that one cycle gait motion timing calculated based on an angle-related signal at one sampling timing is smaller than the currently stored reference cycle gait motion timing and an absolute value of a deviation therebetween is equal to or less than a predetermined threshold, and performs the latest data transmission process in other cases.

In the second aspect, the predetermined threshold is, for example, 90% when the cycle gait motion timing during a gait cycle is 0 to 100%.

In any one of the above various configurations of the gait motion assisting apparatus according to the present invention, the gait motion timing calculating unit has a conversion function specifying a relationship between the thigh phase angle and the cycle gait motion timing during the gait cycle and applies the thigh phase angle transmitted from the thigh phase angle calculating unit to the conversion function to calculate the cycle gait motion timing.

EMBODIMENT FOR CARRYING OUT THE INVENTION

Below, one embodiment of the gait motion assisting apparatus according to the present invention will now be described with reference to the attached drawings.

The gait motion assisting apparatus 100 according to the present embodiment imparts gait assisting force to a user wear a knee-ankle-foot orthosis 1, and is mountable to both the knee-ankle-foot orthosis for left use and the knee-ankle-foot orthosis for right use.

First, the knee-ankle-foot orthosis 1 will now be described taking the knee-ankle-foot orthosis for left use as an example.

Figure 1:
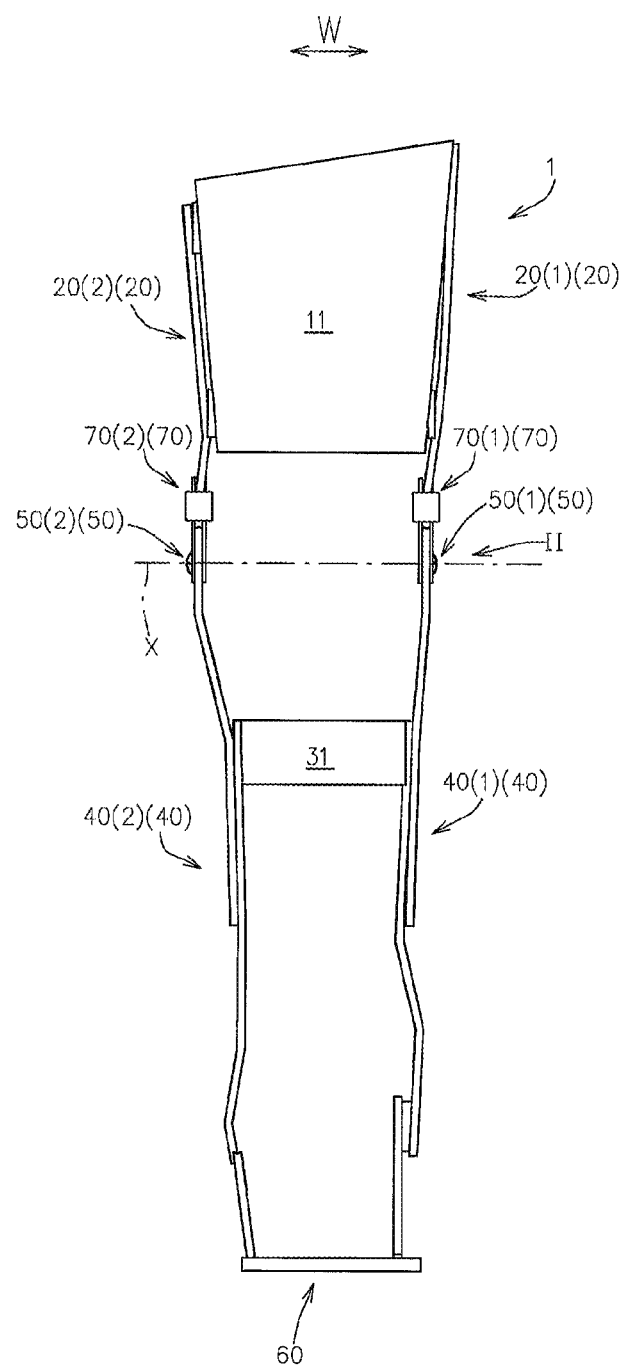
FIG. 1 is a front view of a knee-ankle-foot orthosis to which a gait motion assisting apparatus according to the present invention is attachable.

FIG. 1 is a front view of the knee-ankle-foot orthosis 1 for left use that is attached to the user's left leg.

The knee-ankle-foot orthosis for right use is symmetrical to the knee-ankle-foot orthosis for left use with respect to a central vertical plane passing a body axis of the user and extending in the users front-back direction.

The knee-ankle-foot orthosis 1 is a device to be worn by a person with leg disability or a person with paralysis due to a stroke or the like for gait assistance or for rehabilitation, and is custom-made according to the user's physique.

As shown in FIG. 1, the knee-ankle-foot orthosis 1 has a thigh attachment 11 to which the user's thigh is attached, a thigh frame 20 supporting the thigh attachment 11 and extending in a substantially vertical direction, a lower leg attachment 31 to which the user's lower leg is attached, and a lower leg frame 40 supporting the lower leg attachment 31 and extending in a substantially vertical direction.

The thigh attachment 11 and the lower leg attachment 31 may take various forms as long as they are respectively attachable to the user's thigh and lower leg.

In the present embodiment, the thigh attachment 11 is in a cylindrical form having an attachment hole with such a size that the user's thigh can be inserted and the thigh attachment 11 fits the thigh.

Likewise, the lower leg attachment 31 is in a cylindrical form having an attachment hole with such a size that the user's lower leg can be inserted and the lower leg attachment 31 fits the lower leg.

In the present embodiment, as shown in FIG. 1, the thigh frame 20 has a first thigh frame 20(1) vertically extending on the outer side of the thigh attachment 11 in the user width direction, and a second thigh frame 20(2) vertically extending on the inner side of the thigh attachment 11 in the user width direction.

Likewise, the lower leg frame 40 has a first lower leg frame 40(1) vertically extending on the outer side of the lower leg attachment 31 in the user width direction, and a second lower leg frame 40(2) vertically extending on the inner side of the lower leg attachment 31 in the user width direction.

Figure 2:
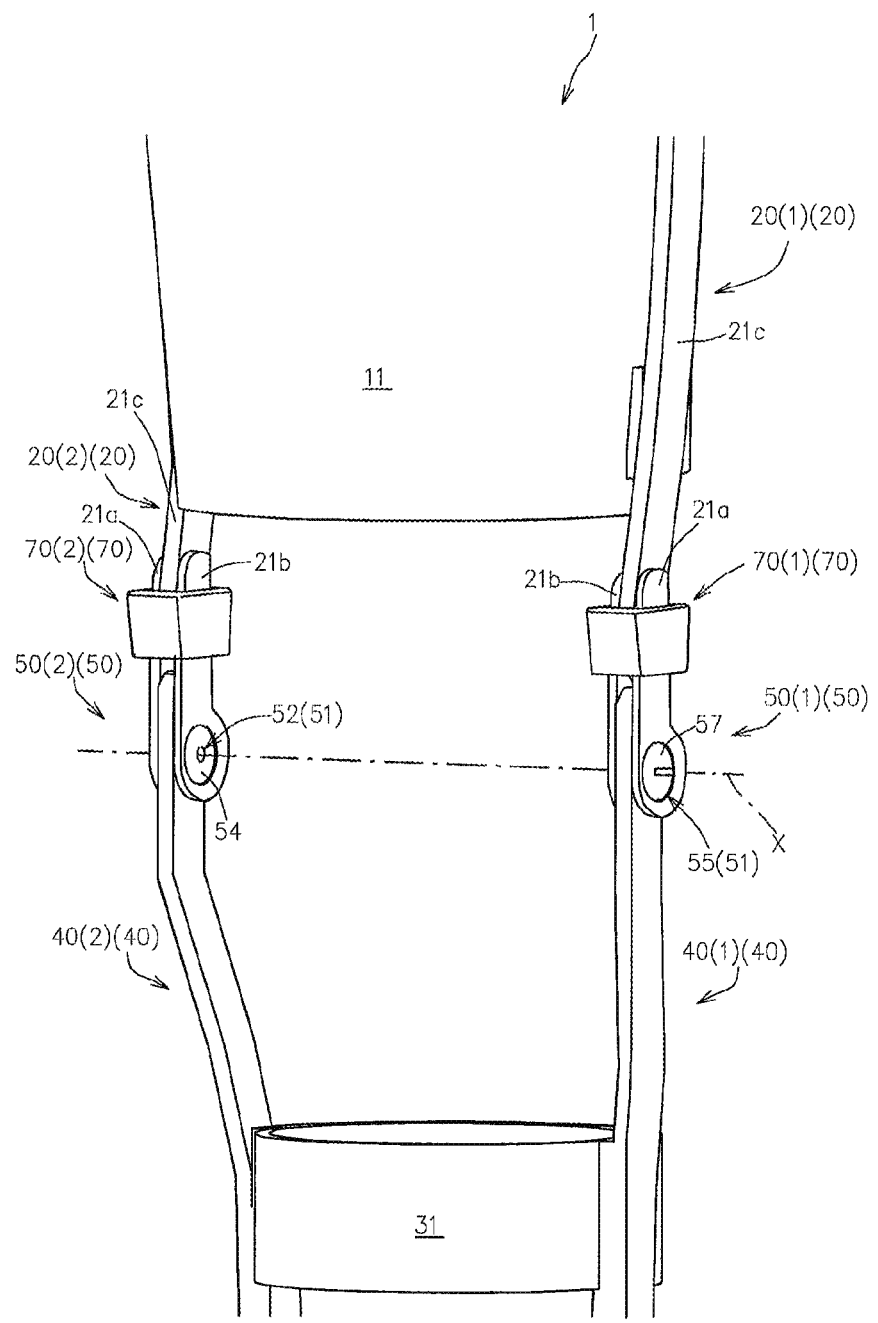
FIG. 2 is a perspective enlarged view of the II part in FIG. 1.

FIG. 2 shows a perspective enlarged view of the II part in FIG. 1.

Figure 3:
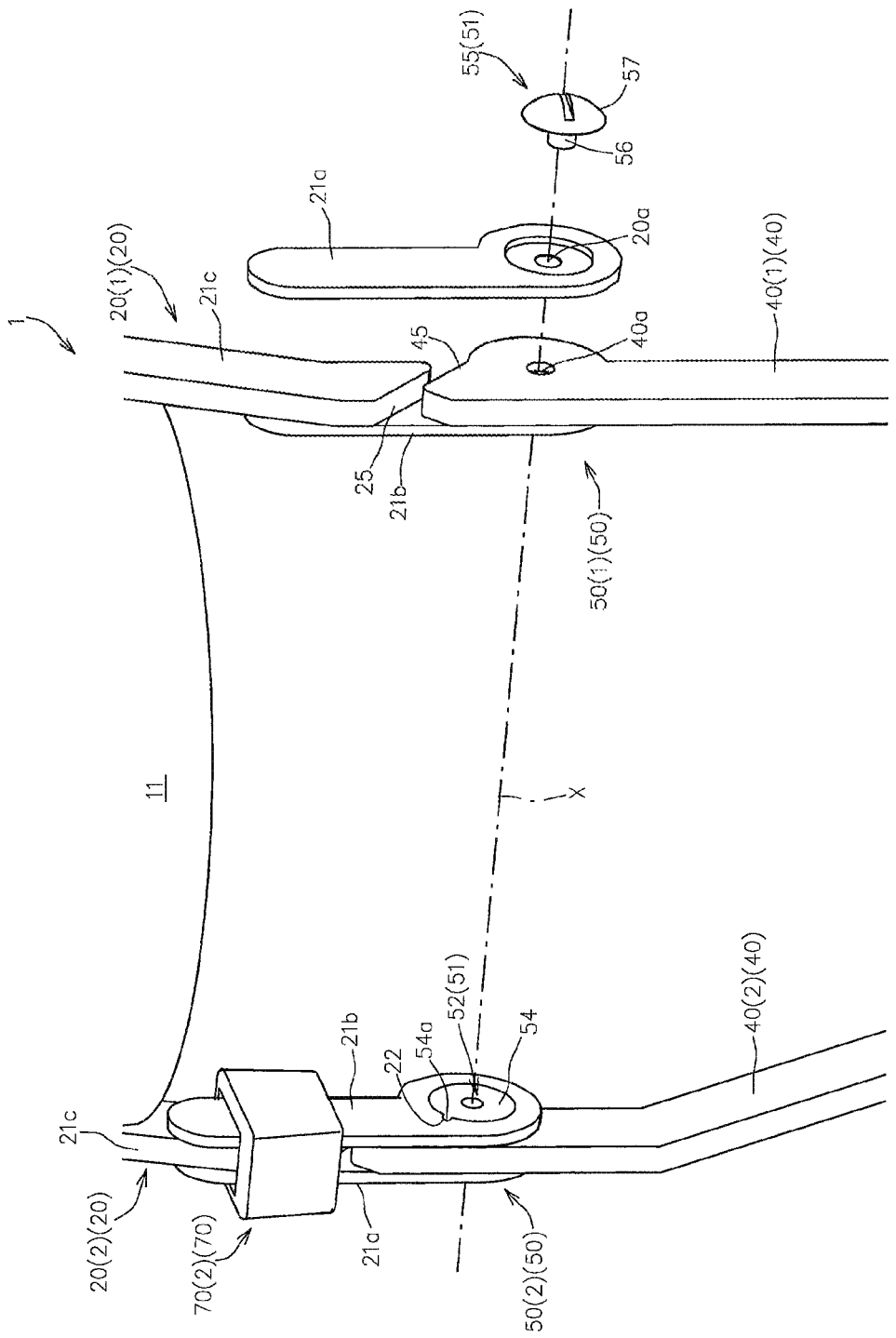
FIG. 3 is an exploded view of FIG. 2.

FIG. 3 shows an exploded perspective view of FIG. 2.

In FIG. 3, illustration of a part of components is omitted for easier understanding.

Figure 4:
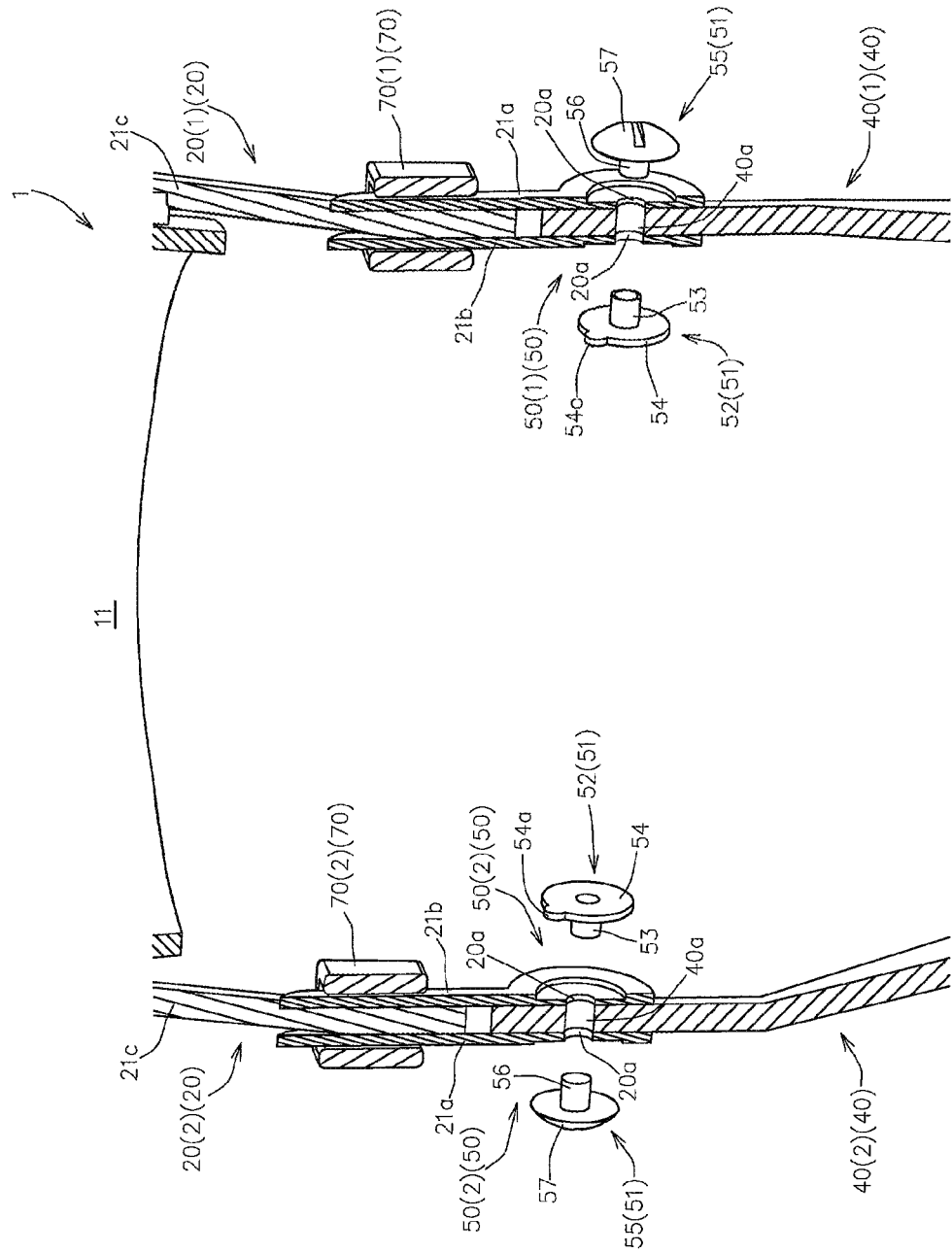
FIG. 4 is a vertical cross-sectional perspective view of FIG. 2.

FIG. 4 shows a vertical cross-sectional perspective view of FIG. 2.

As shown in FIGS. 1 to 4, the lower leg frame 40 is connected to the thigh frame 20 via a brace-side rotational connecting part 50 such that the lower leg frame 40 is rotatable relative to the thigh frame 20 around a brace-side pivot axis line X that is coaxial with the swing axis line of the user's knee joint.

As described above, in the present embodiment, the thigh frame 20 has the first and second thigh frames 20(1), 20(2), and the lower leg frame 40 has the first and second lower leg frames 40(1), 40(2).

In this case, an upper end portion of the first lower leg frame 40(1) is connected to a lower end portion of the first thigh frame 20(1) via a first brace-side rotational connecting part 50(1) so that the first lower leg frame 40(1) is rotatable around the brace-side pivot axis line X relative to the first thigh frame 20(1), and an upper end portion of the second lower leg frame 40(2) is connected to a lower end portion of the second thigh frame 20(2) via a second brace-side rotational connecting part 50(2) so that the second lower leg frame 40(2) is rotatable around the brace-side pivot axis line X relative to the second thigh frame 20(2).

Specifically, as shown in FIGS. 2 to 4, the thigh frame 20 has a vertically extending thigh frame main body 21c and a pair of connecting pieces 21a, 21b fixed to the respective sides in the user width direction of the lower end part of the frame main body 21c by pinning, welding, or the like. The upper part of the lower leg frame 40 is interposed between the pair of connecting pieces 21a, 21b.

The pair of connecting pieces 21a, 21b are provided with a thigh frame attachment hole 20a that is coaxially with the brace-side pivot axis line X, and the lower leg frame 40 is provided with a lower leg frame attachment hole 40a that is coaxially with the brace-side pivot axis line X.

The brace-side rotational connecting part 50 has a brace-side connector 51 for connecting the thigh frame 20 and the corresponding lower leg frame 40 so as to be rotatable around the brace-side pivot axis line X by being inserted into a brace-side frame attachment hole formed by the thigh frame attachment hole 20a and the lower leg frame attachment hole 40a.

As shown in FIGS. 2 to 4, the brace-side connector 51 has an internally threaded member 52 and an externally threaded member 55 separably screwed to each other within the brace-side frame attachment hole.

The internally threaded member 52 has a cylindrical part 53 to be inserted into the brace-side frame attachment hole from one side in the user width direction and a flange part 54 extending more radially outward than the brace-side frame attachment hole from one side in the user width direction of the cylindrical part 53. The cylindrical part 53 has a screw hole that is open toward the free end side.

On the other hand, the externally threaded member 55 has a cylindrical part 56 having an external thread to be screwed into the screw hole from the other side in the user width direction and a flange part 57 extending more radially outward than the brace-side frame attachment hole from the other side in the user width direction of the cylindrical part 56.

As shown in FIGS. 2 to 4, in the present embodiment, the internally threaded member 52 is inserted into the brace-side attachment hole from the side close to the user's thigh inserted into the thigh attachment 11, and the externally threaded member 55 is screwed to the internally threaded member 52 from the side far from the user's thigh.

Reference number 54a in FIGS. 3 and 4 is a radially outward projection that is provided on the flange part 53 and that engages with a depression 22 (see FIG. 3) formed in the inner connecting piece 21b, and thereby the internally threaded member 52 is retained so as to be incapable of relative rotation around the axis line relative to the inner connecting piece 21b (i.e., the thigh frame 20).

In the present embodiment, a swinging position of the lower leg frame 40 around the brace-side pivot axis line X at the time when the user's lower leg is extended until a maximum extending state defines a swinging end of the lower leg frame 40 toward the forward direction around the brace-side pivot axis line X relative to the thigh frame 20.

Specifically, as shown in FIG. 3, an upper-end surface 45 of the lower leg frame 40 (the end surface facing the thigh frame 20) is a sloped surface such that the radial distance from the brace-side pivot axis line X increases from one side toward the other side around the brace-side pivot axis line X, and a lower-end surface 25 of the thigh frame 20 (the end surface facing the lower leg frame 40) is a sloped surface corresponding to the upper-end surface 45 of the lower leg frame 40.

Due to this configuration, at the time when the user's lower leg is extended until a maximum extending state, the lower leg frame 40 rotates only toward one side around the brace-side pivot axis line X relative to the thigh frame 20 (in the direction in which the user's lower leg is bent relative to the thigh) and does not rotate toward the other side (in the direction in which the user's lower leg is extended relative to the thigh).

In the present embodiment, as shown in FIGS. 1 to 4, the knee-ankle-foot orthosis 1 further has a locking member 70 for inhibiting the rotation of the lower leg frame 40 toward both directions around the brace-side pivot axis line X relative to the thigh frame 20.

The locking member 70 is configured so as to be capable of reaching a locked state (the state shown in FIG. 2) where the thigh frame 20 and the lower leg frame 40 are surrounded by the locking member 70 to connect both frames 20, 40 and prevent the lower leg frame 40 from being relatively rotated around the brace-side pivot axis line X relative to the thigh frame 20, and a cancelled state where connection between the thigh frame 20 and the lower leg frame 40 is cancelled to permit the lower leg frame 40 to be relatively rotated around the brace-side pivot axis line X relative to the thigh frame 20.

In the present embodiment, the locking member 70 has a first locking member 70(1) acting on the first thigh frame 20(1) and the first lower leg frame 40(1), and a second locking member 70(2) acting on the second thigh frame 20(2) and the second lower leg frame 40(2).

In the present embodiment, as shown in FIG. 1, the knee-ankle-foot orthosis 1 further has a foot frame 60 on which a user places a foot.

In this case, the lower end portion of the lower leg frame 40 is connected to the foot frame 60.

Below, the gait motion assisting apparatus 100 according to the present embodiment will now be described.

Figure 5:
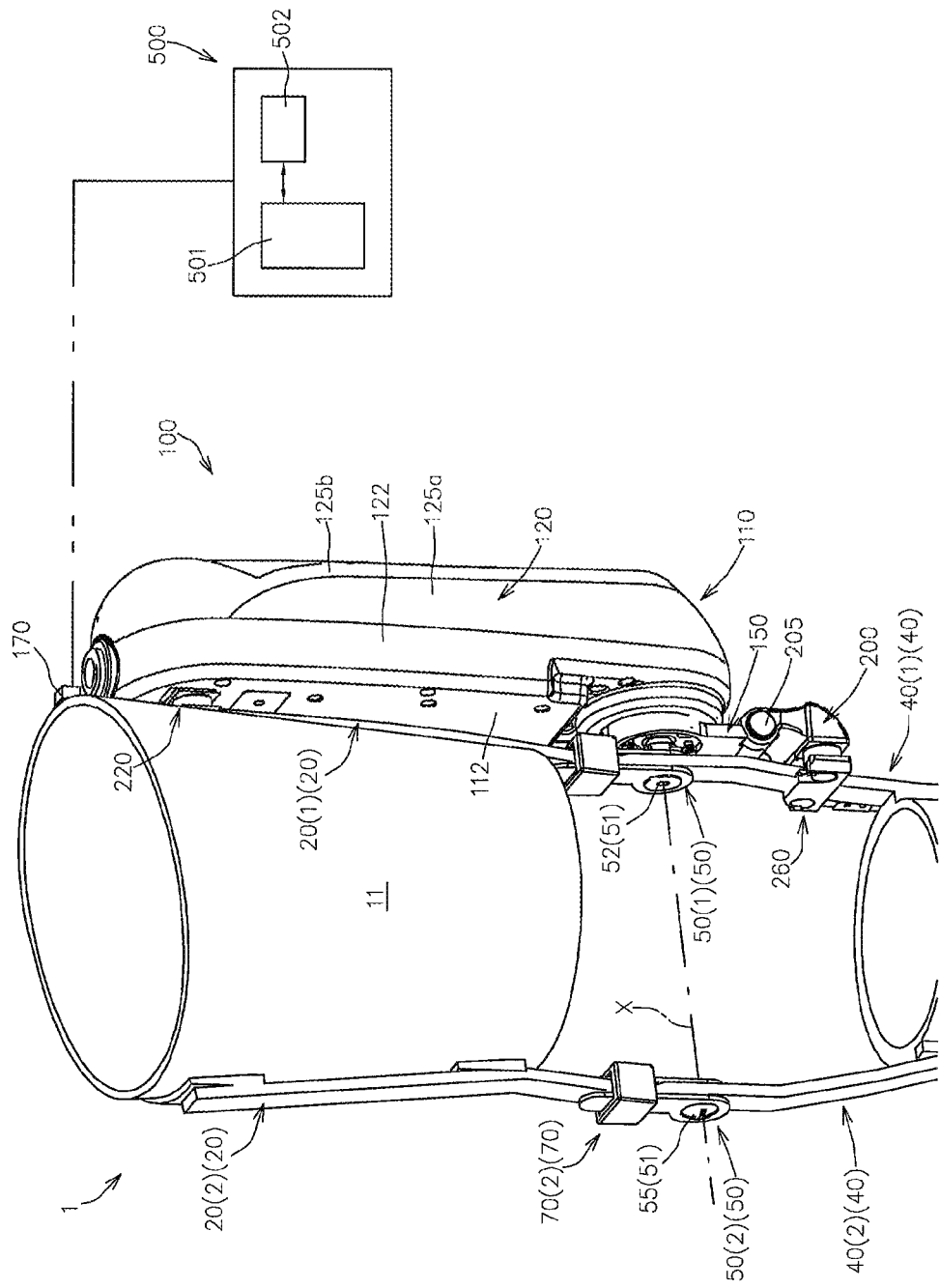
FIG. 5 is a perspective view of an attached state in which a gait motion assisting apparatus according to one embodiment of the present invention is attached to the knee-ankle-foot orthosis as viewed from an inner side in the user width direction and a forward side in the user front-back direction.

FIG. 5 is a perspective view of the gait motion assisting apparatus 100 attached to the knee-ankle-foot orthosis 1 for left use as viewed from the inner side in the user width direction and the forward side in the user front-back direction.

Figure 6:
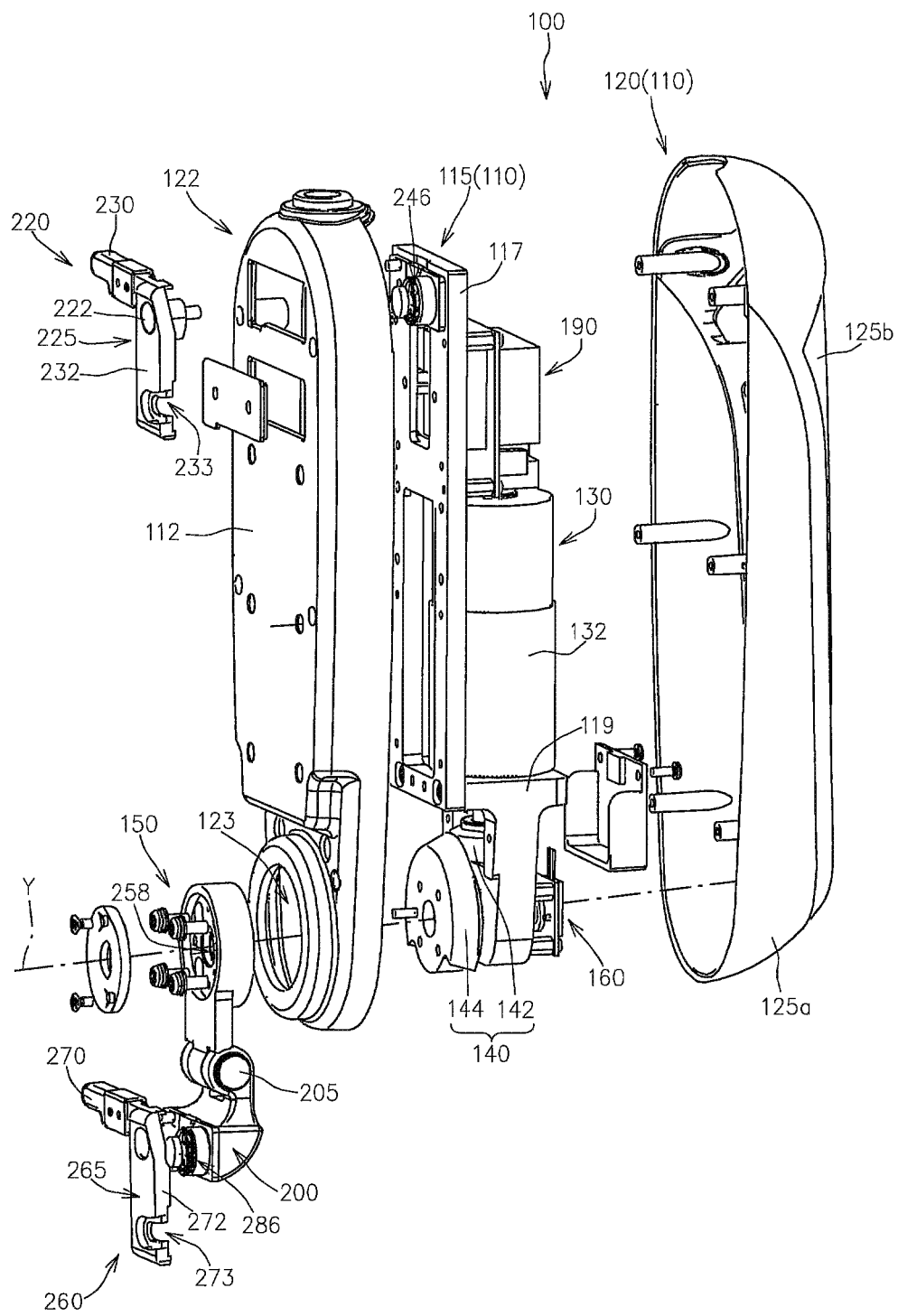
FIG. 6 is an exploded perspective view of the gait motion assisting apparatus as viewed from a side facing the knee-ankle-foot orthosis (the inner side in the user width direction).

FIG. 6 is an exploded perspective view of the gait motion assisting apparatus 100 as viewed from a side facing the knee-ankle-foot orthosis 1.

Figure 7:
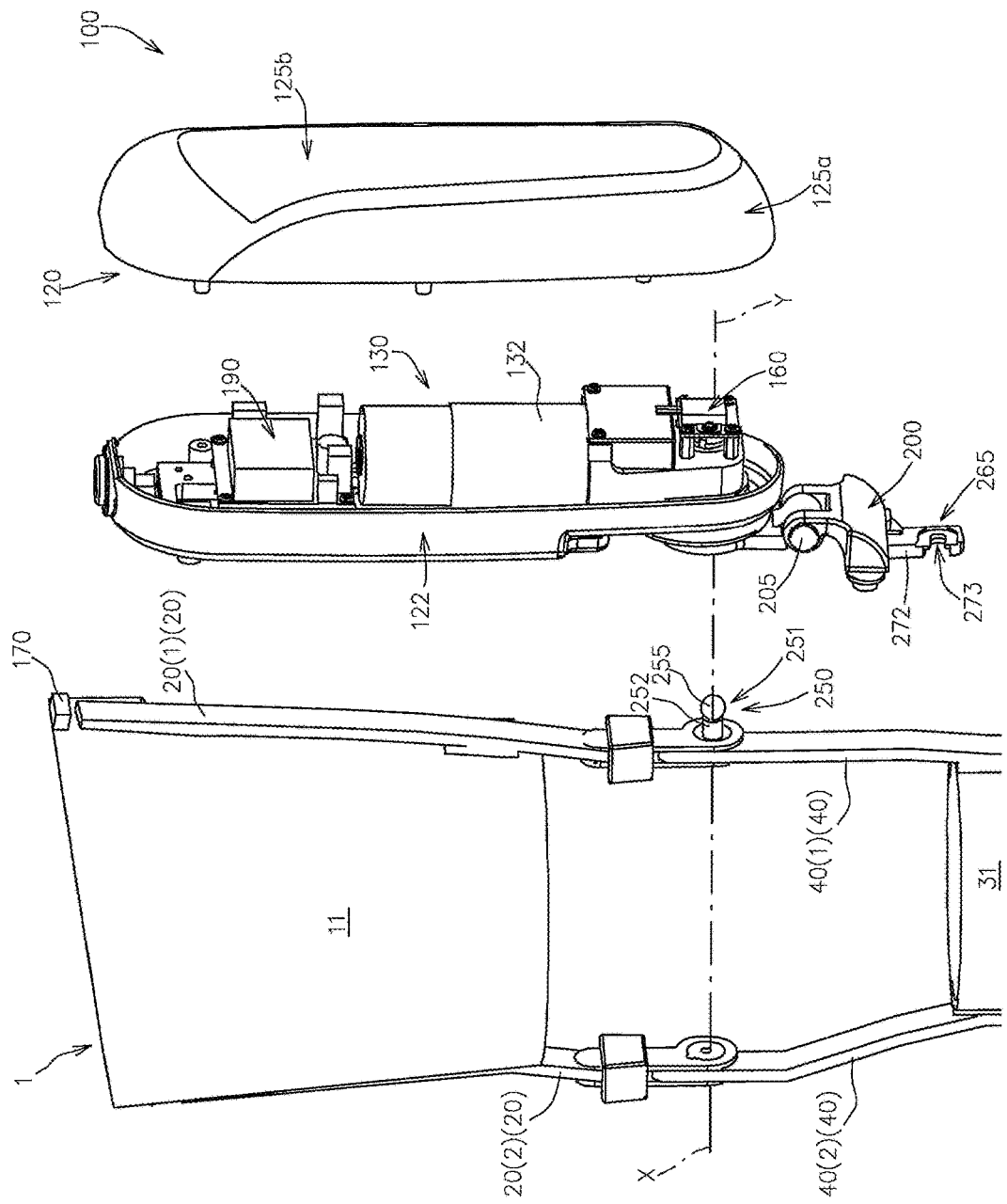
FIG. 7 is an exploded perspective view of the gait motion assisting apparatus and the knee-ankle-foot orthosis as viewed from an outer side in the user width direction.
Figure 8:
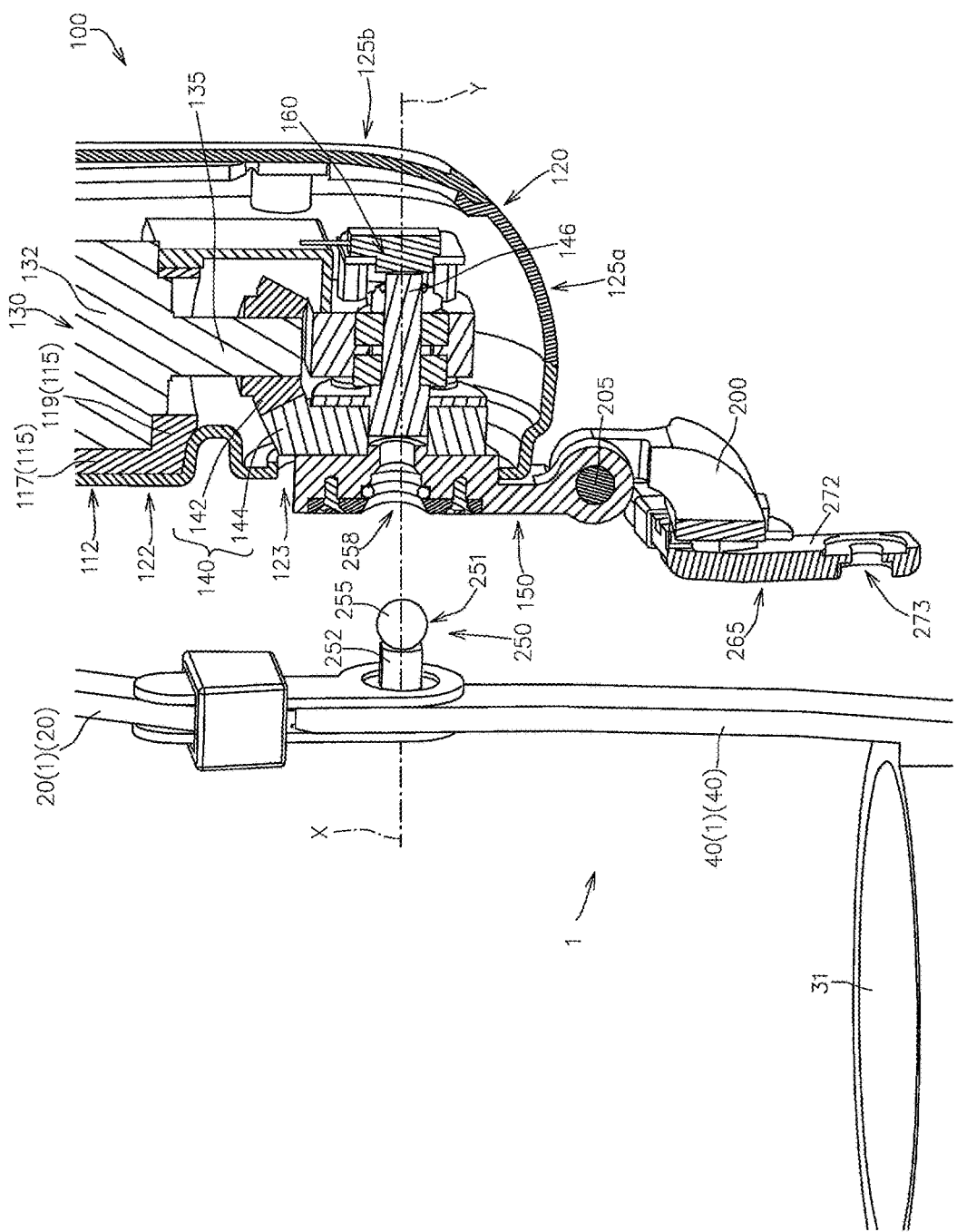
FIG. 8 is an exploded vertical cross-sectional view of the gait motion assisting apparatus and the knee-ankle-foot orthosis.

FIGS. 7 and 8 are an exploded perspective view and an exploded vertical cross-sectional view, respectively, of the gait motion assisting apparatus 100 and the knee-ankle-foot orthosis 1 as viewed from the inner side in the user width direction and the forward side in the user front-back direction.

As shown in FIGS. 5 to 8, the gait motion assisting apparatus 100 includes a casing 110 detachably connected to the knee-ankle-foot orthosis 1, an actuator stored in the casing 110 and outputting gait assisting force for lower leg, a driving arm 150 operatively driven and swung by the actuator, a gait motion state detecting sensor 170 for detecting a gait motion state during a gait cycle, and a control device 500 performing operational control of the actuator.

The casing 110 has a frame 115 supporting the actuator, and a cover 120 surrounding the frame 115 and the actuator.

The frame 115 includes a vertical-direction extending wall 117 extending substantially vertically under the condition where the casing 110 is attached to the knee-ankle-foot orthosis 1, and a horizontal-direction extending wall 119 extending substantially horizontally from the vertical-direction extending wall 117.

The cover 120 includes a lower cover 122 forming a mounting surface 112 that faces the first thigh frame 20(1), and an upper cover 125 detachably connected to the lower cover 122 so as to form an accommodating space that accommodates the frame 115 and the actuator in cooperation with the lower cover 122.

In the present embodiment, the frame 115 is fixed within the accommodating space by connecting the vertical-direction extending wall 117 to an inner surface of the lower cover 122 via fastening members such as bolts.

In the present embodiment, the upper cover 125 includes a first upper cover 125a detachably connected to the lower cover 122, and a second upper cover 125b detachably connected to the first upper cover 125a.

In the present embodiment, an electric motor 130 is utilized as the actuator.

As shown in FIG. 6, the electric motor 130 includes a motor body 132 and an output shaft 135 connected to the motor body 132, and is configured so as to output driving force in both rotational directions including a first direction that is one side around an axial line and a second direction that is the other side around the axial line from the output shaft 135.

In the present embodiment, the motor body 132 is mounted on the horizontal-direction extending wall 119 to be supported by the frame 115. The output shaft 135 extends downward across the horizontal-direction extending wall 119.

As shown in FIGS. 6 and 7, the gait motion assisting apparatus 100 according to the present embodiment further includes a driving source 190 for the electric motor 130 such as a battery.

The driving source 190 is supported by the vertical-direction extending wall 117 so as to be arranged above the electric motor 130.

The drive arm 150 is operatively connected to the output shaft 135, and is swung in a first direction that is one side and a second side that is the other side around an actuator-side pivot axis line Y in response to the driving force in the first and second directions of the output shaft 135.

As shown in FIG. 8, in the present embodiment, the drive arm 150 is operatively connected to the output shaft 135 via a gear transmission mechanism 140.

The gear transmission mechanism 140 includes a driving-side bevel gear 142 supported by the output shaft 135 so as to be incapable of relative rotation, and a driven-side bevel gear 144 arranged coaxially with the actuator-side pivot axis line Y while being engaged with the driving-side bevel gear 142.

The driven-side bevel gear 144 is arranged closer to the knee-ankle-foot orthosis 1 in the user width direction W than the output shaft 135 is.

The proximal end portion of the drive arm 150 is connected to the driven-side bevel gear 144 so that the drive arm 150 is swung around the actuator-side pivot axis line Y in response to the driving power of the output shaft 135.

As shown in FIG. 8, the lower cover 122 is provided with an access opening 123. The driven-side bevel gear 144 and the proximal end portion of the drive arm 150 are connected to each other via the access opening 123.

A distal end portion of the drive arm 150 is operatively connected to the first lower leg frame 40(1) in a state that the gait motion assisting apparatus 100 is attached to the knee-ankle-foot orthosis 1 so that the drive arm 150 presses the first lower leg frame 40(1) around the brace-side pivot axis line X in response to the swing of the drive arm 150 around the actuator-side pivot axis line Y.

The gait motion assisting apparatus 100 according to the present embodiment further includes a rotation angle sensor 160 for detecting a swinging position of the drive arm 150.

Specifically, a detected shaft 146 is connected to the driven-side bevel gear 144 so as to be incapable of relative rotation around the actuator-side pivot axis line Y. The rotation angle sensor 160 is arranged to detect a rotation angle of the detected shaft 146 around the axis line.

The gait motion assisting apparatus 100 is detachably mounted to the knee-ankle-foot orthosis 1 at three portions including an upper portion, lower portion and an intermediate portion between the upper and lower portions in the vertical direction.

Specifically, as shown in FIG. 6, the gait motion assisting apparatus 100 includes an upper connecting mechanism 220, a lower connecting mechanism 260 and an intermediate connecting mechanism 250.

As shown in FIG. 8, the intermediate connecting mechanism 250 includes a ball stud 251 arranged at the knee-ankle-foot orthosis 1, and an accommodation depression 258 that is arranged at the gait motion assisting apparatus 100 so that the ball stud 251 and the accommodation depression 258 forms a ball joint structure.

As shown in FIG. 8, the ball stud 251 includes a shaft part 252 positioned coaxially with the brace-side pivot axis line X of the knee-ankle-foot orthosis 1 and extending in a direction toward the gait motion assisting apparatus 100, and a spherical head part 255 provided at the distal end portion of the shaft part 252.

In the present embodiment, the ball stud 251 is provided on the knee-ankle-foot orthosis 1 in a projecting manner by utilizing the brace-side connector 51.

Specifically, as shown in FIGS. 4 and 8, the ball stud 251 is provided on the knee-ankle-foot orthosis 1 in a projecting manner by being screw-connected to an inner-side threaded member (the internally threaded member 52 in the present embodiment) positioned on the inner side in the user width direction among the internally threaded member 52 and the externally threaded member 55 in the swinging connector 51, in place of an outer-side threaded member (the externally threaded member 55 in the present embodiment) positioned on the outer side in the user width direction among the internally threaded member 52 and the externally threaded member 55.

The ball stud 251 and the inner-side threaded member are realized by various configurations.

For example, the ball stud 251 may be formed with an axial stepped hole passing through in the axial line direction. The axial stepped hole includes a large-diameter portion open toward a side on which the spherical head part 255 is positioned, a small-diameter portion open toward a side far away from the spherical head part 255 in the axial line direction, and a step connecting the large-diameter portion and the small-diameter portion. The ball stud 251 and the inner-side threaded member can be connected to each other by a fastening member such as a bolt inserted in the axial stepped hole and fastened to the inner-side threaded member.

According to this configuration, the ball stud 251 can be easily provided on the existing knee-ankle-foot orthosis 1 in a projecting manner so as to be coaxial with the brace-side pivot axis line X.

In the present embodiment, as shown in FIG. 8, the accommodation depression 258 is formed in the proximal end portion of the drive arm 150.

The configuration makes it possible to stably cause the brace-side pivot axis line X and the actuator-side pivot axis line Y to be arranged coaxially with each other while reducing the size of the gait motion assisting device 100A in the user width direction.

As shown in FIG. 6, the upper connecting mechanism 220 includes an upper rotational shaft 222 provided on the mounting surface 112 so as to extend inward in the user width direction and an upper fastening member 225 supported by the upper rotational shaft 222 so as to be rotatable around an axis line of the upper rotational shaft 222.

The upper fastening member 225 includes a bearing part 227 supported by the upper rotational shaft 222 and a cam part 229 extending radially outward from the bearing part 227.

The cam part 229 is configured such that the radial distance between the outer circumferential surface of the cam part 229 and the axis line of the upper rotational shaft 222 is increased toward a first side around the axis line of the upper rotational shaft 222.

The upper connecting mechanism 220 further includes an upper receiving member 246 provided on the mounting surface 112 at a position spaced apart in the user front-back direction from the upper rotational shaft 222 by a distance that enables the first thigh frame 20(1) to be interposed between the upper receiving member 246 and the upper rotational shaft 222.

In the present embodiment, the upper connecting mechanism 220 includes an upper receiving shaft 247 provided on the mounting surface 112 so as to extend inward in the user width direction, and an elastic roller 248 supported by the upper receiving shaft 247 acts as the upper receiving member 246.

In the state where the upper fastening member 225 is positioned in the releasing position around the upper rotational shaft 222, moving the gait motion assisting device 100 in a direction toward the knee-ankle-foot orthosis 1 enables the first thigh frame 20(1) to be positioned in the space between the upper fastening member 225 and the upper receiving member 246, and in the state where the first thigh frame 20(1) is positioned in the space, moving the gait motion assisting device 100 in a direction away from the knee-ankle-foot orthosis 1 enables the first thigh frame 20(1) to be retreated from the space.

Moreover, in the state where the first thigh frame 20(1) is positioned in the space, rotating the upper fastening member 225 from the releasing position to a fastening position around the upper rotational shaft 222 causes the cam part 229 to hold the first thigh frame 20(1) in cooperation with the upper receiving member 246 with respect to the user front-back direction, and thereby the state where the upper part of the gait motion assisting device 100 is connected to the first thigh frame 20(1) is attained.

As shown in FIG. 6, in the present embodiment, the upper fastening member 225 further includes an operation arm 230 extending radially outward from the bearing part 227.

The operation arm 230 is configured such that the radial length between the free end of the operation arm 230 and the axis line of the upper rotational shaft 222 is greater than the radial length between the radially outermost end of the cam part 229 and the axis line of the upper rotational shaft 222.

This configuration, while making it easy to rotate the upper fastening member 225 around the upper rotational shaft 222 via the operation arm 230, makes it possible to effectively prevent connection between the upper part of the gait motion assisting device 100A and the first thigh frame 20(1) from being cancelled by the rotation of the upper fastening member 225 around the upper rotational shaft 222 via the cam part 229 when external force is unintentionally applied to the first thigh frame 20(1) and the upper part of the gait motion assisting device 100.

As shown in FIG. 6, in the present embodiment, the upper fastening member 225 has an engagement arm 232 extending radially outward from the bearing part 227 on the inner side in the user width direction than the cam part 229.

The engagement arm 232 is provided on the upper fastening member 225 so as to be positioned on the inner side in the user width direction than the first thigh frame 20(1) positioned in the space between the upper fastening member 225 and the upper receiving member 246.

The engagement arm 232 is provided with an engagement groove 233 for engagement with a portion of the upper receiving shaft 247, which extends more inward in the user width direction than the upper receiving member 246, when the upper fastening member 225 is rotated around the upper rotational shaft 222 from the releasing position to the fastening position around upper rotational shaft 222 so that the cam part 229 holds the first thigh frame 20(1) with respect to the user front-back direction in cooperation with the upper receiving member 246, and by the inward extending portion of the upper receiving shaft 247 inserted in the engagement groove 233, the unintentional relative movement of the upper part of the gait motion assisting device 100 and the first thigh frame 20(1) in the user width direction is prevented.

Next, the lower connecting mechanism 260 will be now described.

As shown in FIGS. 5 to 8, in the present embodiment, the distal end portion of the drive arm 150 is provided with a swinging member 200 capable of swinging around a rotational shaft 205 along the user front-back direction, and the lower connecting mechanism 260 is provided in the swinging member 200.

The configuration makes it possible to appropriately change the relative position of the lower connecting mechanism 260 with respect to the upper connecting mechanism 220 and the intermediate connecting mechanism 250 in the user width direction so that the gait motion assisting device 100 can be appropriately attached to the variously shaped knee-ankle-foot orthoses 1 that are custom-made according to the user's physique.

That is, the knee-ankle-foot orthosis 1 is custom-made according to the user's physique, and thus the tilt angle and/or the curvature of the first thigh frame 20(1) relative to the first lower leg frame 40(1) with respect to the user width direction W (see FIG. 1) is different for each knee-ankle-foot orthosis 1.

In this regard, adopting the configuration in which the swinging member 200 is connected to the distal end portion of the drive arm 150 so as to be capable of swinging in the user width direction and the lower connecting mechanism 260 is provided in the swinging member 200 enables the gait motion assisting device 100 to be appropriately attached to various knee-ankle-foot orthoses 1 having different tilt angles and/or curvatures of the first thigh frame 20(1) relative to the first lower leg frame 40(1) with respect to the user width direction W.

The lower connecting mechanism 260 has the substantially same configuration as the upper connecting mechanism 220.

Specifically, as shown in FIG. 6, the lower connecting mechanism 260 includes a lower rotational shaft 262 provided on the swinging member 200 so as to extend inward in the user width direction and a lower fastening member 265 supported by the lower rotational shaft 262 so as to be rotatable around an axis line of the lower rotational shaft 262.

The lower fastening member 265 includes a bearing part (not shown) supported by the lower rotational shaft 262 and a cam part (not shown) extending radially outward from the bearing part.

The cam part is configured such that the radial distance between the outer circumferential surface of the cam part and the axis line of the lower rotational shaft 262 is increased toward a first side around the axis line of the lower rotational shaft 262.

As shown in FIG. 6, the lower connecting mechanism 260 further includes a lower receiving member 286 supported by the swinging member 200 at a position spaced apart in the user front-back direction from the lower rotational shaft 262 by a distance that enables the first lower leg frame 40(1) to be interposed between the lower receiving member 286 and the lower rotational shaft 262.

In the present embodiment, the lower connecting mechanism 260 includes a lower receiving shaft 287 provided on the swinging member 200 so as to extend inward in the user width direction, and an elastic roller 288 supported by the lower receiving shaft 287 acts as the lower receiving member 286.

In the state where the lower fastening member 265 is positioned in the releasing position around the lower rotational shaft 262, moving the gait motion assisting device 100 in a direction toward the knee-ankle-foot orthosis 1 enables the first lower leg frame 40(1) to be positioned in the space between the lower fastening member 265 and the lower receiving member 286, and in the state where the first lower leg frame 40(1) is positioned in the space, moving the gait motion assisting device 100 in a direction away from the knee-ankle-foot orthosis 1 enables the first lower leg frame 40(1) to be retreated from the space.

Moreover, in the state where the first lower leg frame 40(1) is positioned in the space, rotating the lower fastening member 265 from the releasing position to a fastening position around the lower rotational shaft 262 causes the cam part to hold the first lower leg frame 40(1) in cooperation with the lower receiving member 286 with respect to the user front-back direction, and thereby the state where the lower part of the gait motion assisting device 100 is connected to the first lower leg frame 40(1) is attained.

As shown in FIG. 6, in the present embodiment, the lower fastening member 265 further includes an operation arm 270 extending radially outward from the bearing part 267.

The operation arm 270 is configured such that the radial length between the free end of the operation arm 270 and the axis line of the lower rotational shaft 262 is greater than the radial length between the radially outermost end of the cam part 269 and the axis line of the lower rotational shaft 262.

This configuration, while making it easy to rotate the lower fastening member 265 around the lower rotational shaft 262 via the operation arm 270, makes it possible to effectively prevent connection between the lower part of the gait motion assisting device 100 and the first lower leg frame 40(1) from being cancelled by the rotation of the lower fastening member 265 around the lower rotational shaft 262 via the cam part 269 when external force is unintentionally applied to the first lower leg frame 40(1) and the lower part of the gait motion assisting device 100.

As shown in FIG. 6, in the present embodiment, the lower fastening member 265 has an engagement arm 272 extending radially outward from the bearing part 267 on the inner side in the user width direction than the cam part 269.

The engagement arm 272 is provided on the lower fastening member 265 so as to be positioned on the inner side in the user width direction than the first lower leg frame 40(1) positioned in the space between the lower fastening member 265 and the lower receiving member 286.

The engagement arm 272 is provided with an engagement groove 273 for engagement with a portion of the lower receiving shaft 287, which extends more inward in the user width direction than the lower receiving member 286, when the lower fastening member 265 is rotated around the lower rotational shaft 262 from the releasing position to the fastening position around lower rotational shaft 262 so that the cam part 269 holds the first lower leg frame 40(1) with respect to the user front-back direction in cooperation with the lower receiving member 286, and by the inward extending portion of the lower receiving shaft 287 inserted in the engagement groove 273, the unintentional relative movement of the lower part of the gait motion assisting device 100 and the first lower leg frame 40(1) in the user width direction is prevented.

Next, the control structure of the gait motion assisting device 100 will now be described.

Figure 9:
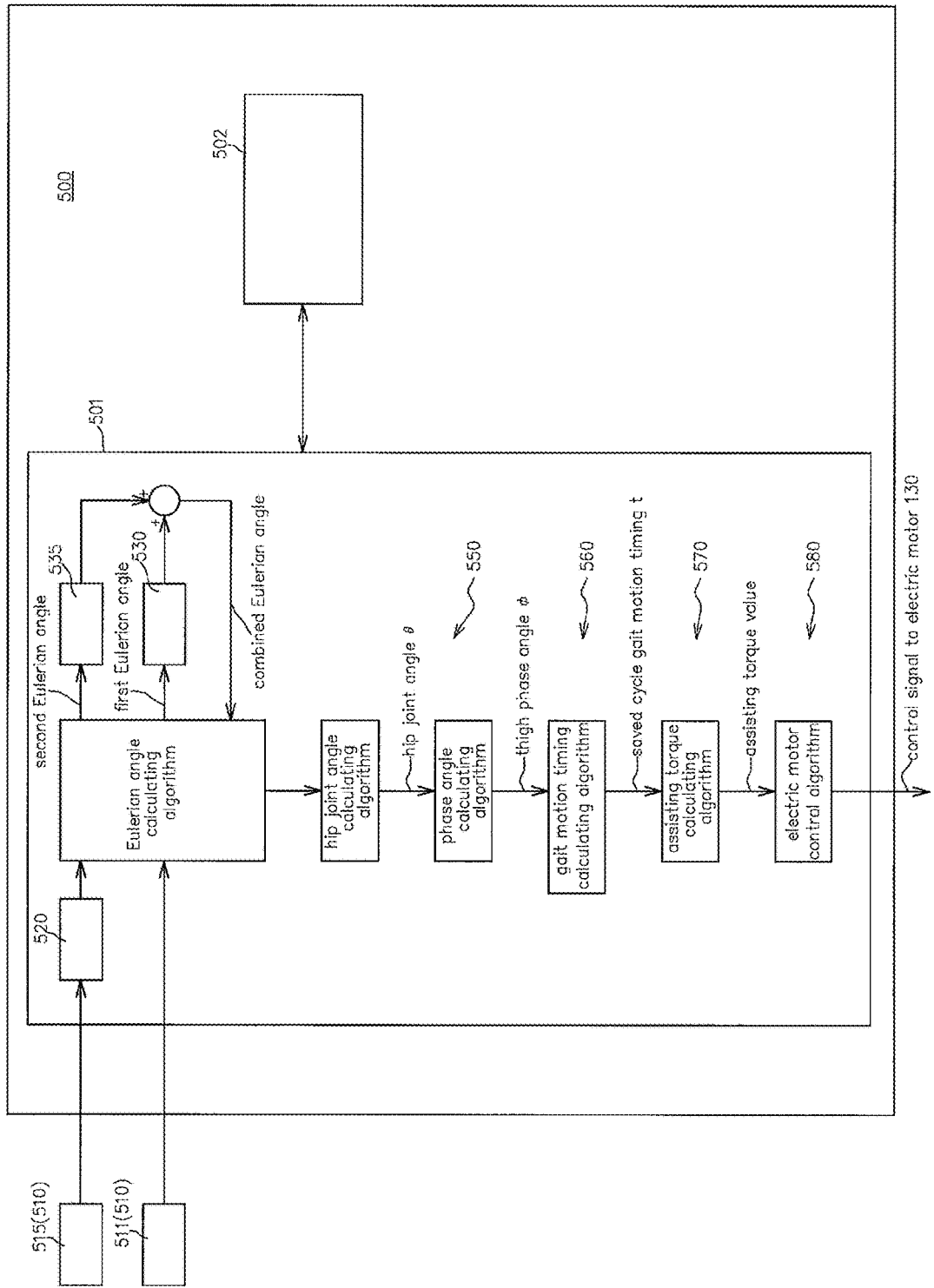
FIG. 9 is a control block diagram of the gait motion assisting apparatus.

FIG. 9 shows a control block diagram of the gait motion assisting device 100.

The gait motion assisting device 100 includes a thigh orientation detecting unit 510 as the gait motion state detecting sensor 170, and recognizes a gait state during gait cycle (a cycle gait motion timing) based on a thigh phase angle $\varphi$ and performs operational control for the electric motor 130 such that gait assisting force suitable for the gait state is imparted.

That is, the gait motion assisting device 100 is configured to detect movement of not the lower leg that is a control target site but the thigh that is a site different from the lower leg, recognize the gait state during gait cycle based on the movement of the thigh, and impart a gait assisting force in accordance with the gait state to the lower leg that is an assisting force imparted target site.

Specifically, the thigh orientation detecting unit 510 is capable of detecting an angle-related signal relating to a hip joint angle that is the front-back swing angle of the user's thigh at each sampling point.

In addition, as shown in FIG. 9, the gait motion assisting device 100 includes a thigh phase angle calculating unit 550 that calculates a thigh phase angle based on the angle-related signal, an assisting torque calculating unit 570 that calculates a torque value that should be output at the gait state recognized based on the thigh phase angle φ, and an operational control unit 580 responsible for operational control for the actuator.

As shown in FIG. 9, the gait motion assisting device 100 according to the present embodiment includes a gait motion timing calculating unit 560 for calculating a gait state during gait cycle corresponding to the thigh phase angle φ (that is, a cycle gait motion timing that is defined using a percentage relative to the gait cycle). The assisting torque calculating unit 570 is configured to calculate, based on the cycle gait motion timing, a torque value to be output.

The assisting torque calculating unit 570 has an output torque pattern defining a relationship between a cycle gait motion timing during a gait cycle and a torque value to be output, and applies a cycle gait motion timing calculated by the gait motion timing calculating unit 560 to the output torque pattern to calculate the torque value to be output.

As shown in FIG. 9, in the gait motion assisting device 100 according to the present embodiment, the control device 500 acts as the thigh phase angle calculating unit 550, the gait motion timing calculating unit 560, the assisting torque calculating unit 570 and the operational control unit 580.

Specifically, the control device 500 has a control part 501 including a control processing unit for executing processing based on a signal received from the thigh orientation detecting unit 510, a manually operated member or the like; and a storage part 502 including a ROM storing a control program, control data and the like, a non-volatile storage unit storing a setting value or the like such that the setting value or the like is not lost even when a power supply is interrupted and is rewritable, a RAM temporarily storing data generated during processing by the processing part or the like.

The thigh orientation detecting unit 510 detects the angle-related signal at each predetermined specific sampling timing during gait cycle.

The thigh orientation detecting unit 510 may have various forms such as a gyro sensor, an acceleration sensor, a rotary encoder and a sensor measuring muscle current and hardness of muscle as long as it can directly or indirectly detect the front-back swing angle of the thigh (the hip joint angle θ).

In the gait motion assisting device 100 according to the present embodiment, the thigh orientation detecting unit 510 has a triaxial angular velocity sensor (a gyro sensor) 511 (see FIG. 9) capable of detecting the front-back swing angle velocity of the thigh. The thigh phase angle calculating unit 550 integrates the angular velocity of the thigh detected by the triaxial angular velocity sensor 511 so that the hip joint angle θ, which is the front-back swing angle of the thigh, is obtained.

The gait motion assisting apparatus according to the present embodiment is provided with a triaxial acceleration sensor 515, and the thigh phase angle calculating unit 550 is configured to calculate the hip joint angle (the front-back swing angle of the thigh) with using the vertical axis line that the triaxial acceleration sensor 515 detects when the user is in a standstill as the reference value.

Instead, the gait motion assisting apparatus can be configured not to have the triaxial acceleration sensor 515.

In this case, the hip joint angle θ (the front-back swing angle of the thigh) calculated by the thigh phase angle calculating unit 550 is the thigh front-back swing angle with an angle that the thigh phase angle calculating unit 550 calculates when the main power source of the gait motion assisting apparatus 100 is turned on as the reference value.

Thus, in this case, the thigh phase angle calculating unit 550 can correct the hip joint angle θ (the front-back swing angle of the thigh) by using a high-pass filter so that the median value of the hip joint angle θ is the reference value thereof.

Alternatively, instead of using a high pass filter, the thigh phase angle calculating unit 550 can detect a deviation between the maximum value in the positive direction and the maximum value in the negative direction of a calculated hip joint angle θ (front-back swing angle of the thigh) and, based on the deviation, correct calculated hip joint angle so that the median value of the hip joint angle is the reference values thereof.

While it is also possible to detect the front-back swing angle of the thigh relative to the body axis line by a rotary encoder and use the detected value as a hip joint angle θ, in the present embodiment, the hip joint angle is calculated based on an angular velocity detected by the triaxial angular velocity sensor 511, and thereby the degree of design freedom of the gait motion assisting apparatus 100 is increased.

That is, in a case where the hip joint angle θ (the thigh front-back swing angle relative to the body axis line) is detected by a rotary encoder, it is necessary to detect the angle of relative movement between a torso-side detector secured to the torso and a thigh-side detector secured to the thigh so as to swing integrally with the thigh, and it is therefore necessary to attach both detectors such that the torso-side detector and the thigh-side detector do not positionally shift relative to the torso and the thigh, respectively.

On the other hand, the method of calculating a hip joint angle based on an angular velocity detected by the triaxial angular velocity sensor 511 does not have the above-described restrictions and can provide enhanced design freedom of the gait motion assisting apparatus 100.

As described above, in the gait motion assisting apparatus 100 according to the present embodiment, the thigh orientation detecting unit 510 has the triaxial acceleration sensor 515 in addition to the triaxial angular velocity sensor 511.

In this case, the thigh phase angle calculating unit 550 is configured to calculate a combined Eulerian angle by combining a high-frequency component of a first Eulerian angle calculated based on angular velocity data from the triaxial angular velocity sensor 511 and a low-frequency component of a second Eulerian angle calculated based on acceleration data from the triaxial acceleration sensor 515, and calculate a thigh phase angle φ based on a hip joint angle θ calculated from the combined Eulerian angle and a hip joint angular velocity ω calculated from the hip joint angle θ.

Specifically, as shown in FIG. 9, the thigh phase angle calculating unit 550 receives sensor coordinate axis-based angular velocity data from the triaxial angular velocity sensor 511 at every sampling timing, and converts the angular velocity data into angular velocity data (Eulerian angular velocity) that indicates a correlation between a sensor coordinate axis and a global coordinate axis (a vertical direction-based spatial coordinate axis) using a predetermined conversion formula.

Then, the thigh phase angle calculating unit 550 integrates the angular velocity data (Eulerian angular velocity) to calculate the first Eulerian angle.

Preferably, the thigh phase angle calculating unit 550 can perform drift elimination on sensor coordinate axis-based angular velocity data received from the triaxial angular velocity sensor 511 at every predetermined sampling timing using angular velocity data received from the triaxial angular velocity sensor 511 when the user is in standstill (or when the user is not in motion).

Moreover, the thigh phase angle calculating unit 550 receives sensor axis-based acceleration data from the triaxial acceleration sensor 515 at every sampling timing via a low-pass filter 520, and calculates the second Eulerian angle indicating a correlation between a sensor coordinate axis and a global coordinate axis (a vertical direction-based spatial coordinate axis) from the acceleration data received via the low-pass filter 520, based on acceleration data received when the user is in standstill and gravitational acceleration.

Then, the thigh phase angle calculating unit 550 calculates a hip joint angle θ from a unit vector indicating the orientation of the thigh and the combined Eulerian angle obtained by combining the high-frequency component of the first Eulerian angle obtained via a high-pass filter 530 and the low-frequency component of the second Eulerian angle obtained via the low-pass filter 535.

Preferably, the thigh phase angle calculating unit 550 can perform drift elimination by detecting heel contact based on acceleration data from the acceleration sensor 515 and, when heel contact is detected, adding a corrected Eulerian angle calculated from angular velocity data from the triaxial angular velocity sensor 511 to the combined Eulerian angle.

A thigh phase angle φ is calculated by the following algorithm.

The thigh phase angle calculating unit 550, at every sampling timing, calculates a hip joint angle θ and, also, differentiates it to calculate a hip joint angular velocity ω.

For example, the thigh phase angle calculating unit 550 calculates a hip joint angle θ(k) at the $k^{th}$ sampling timing S(k) (k is an integer of 1 or greater) from a gait cycle reference timing, and then differentiates it to calculate a hip joint angular velocity ω(k) at the sampling timing S(k).

The gait cycle reference timing can be set, for example, at a timing of heal contact or a timing after a predetermined time from heel contact.

The timing of heel contact can be recognized by various methods.

For example, if the hip joint angular velocity ω when the thigh swings forward and backward based on the vertical axis line is referred to as positive and negative, respectively, a time point at which the calculated hip joint angular velocity ω advances by a predetermined phase angle Δα from a timing at which the calculated hip joint angular velocity ω reaches zero from a positive value can be recognized as the heel contact timing Alternatively, it is possible to provide the gait motion assisting apparatus 100 with a heel contact detecting unit for detecting heel contact, and configure the thigh phase angle detecting unit 550 to recognize a timing detected by the heel contact detecting unit as a heel contact time point. The heel contact detecting unit may be formed by a pressure sensor capable of detecting ground contact of the heel.

Moreover, in a case where the acceleration sensor 515 is provided as in the gait motion assisting apparatus 100 according to the present embodiment, the acceleration sensor 515 can also be used as the heel contact detecting unit.

Then, the thigh phase angle calculating unit 550 calculates a thigh phase angle φ(k) (=−Arctan(ω(k)/θ(k))) at the sampling timing S(k) based on the hip joint angle θ(k) and the hip joint angular velocity ω(k) at the sampling timing S(k).

Figure 10:
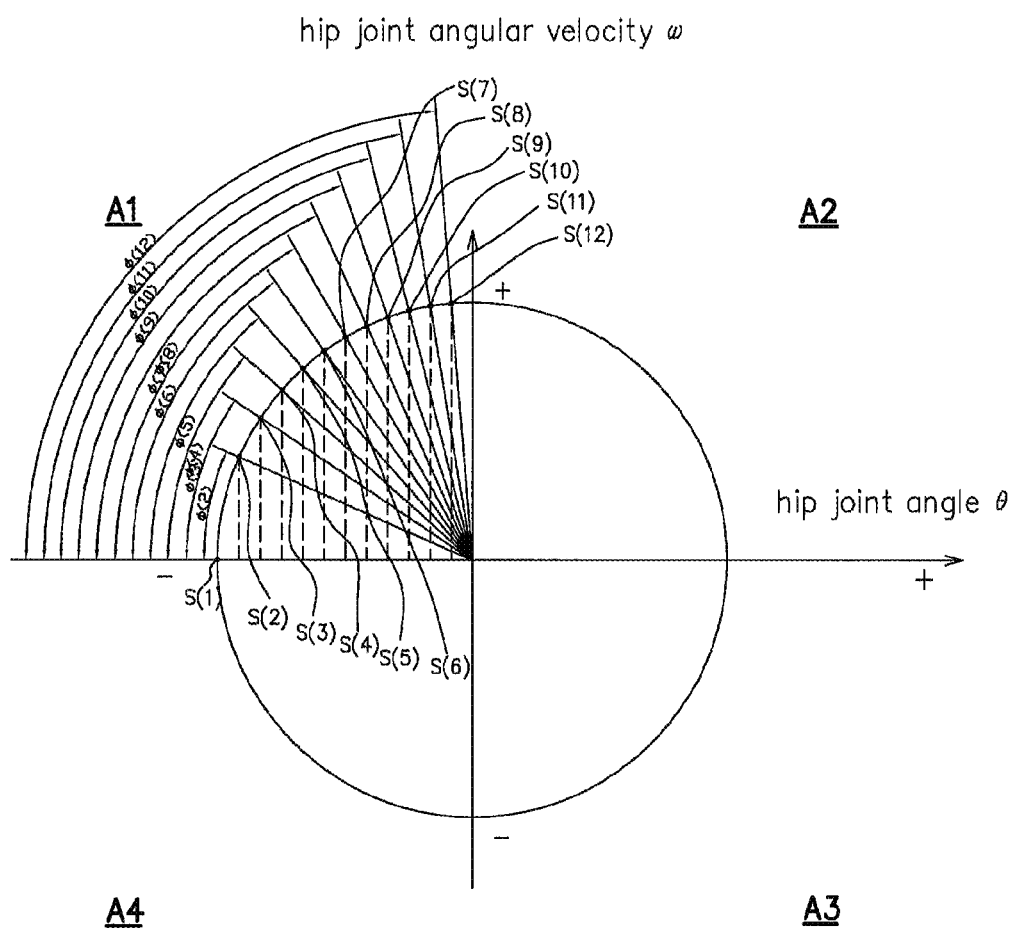
FIG. 10 is a trajectory diagram obtained by plotting hip joint angles θ and hip joint angular velocities ω over a gait cycle in a state where the scale (amplitude) of the hip joint angle θ matches the scale (amplitude) of the hip joint angular velocity ω, the angles θ and the velocities ω being calculated by a control device of the gait motion assisting apparatus.

FIG. 10 schematically illustrates a trajectory diagram obtained by plotting the thigh phase angle φ (gait state), which is defined by the hip joint angle θ and the hip joint angular velocity ω, over a gait cycle.

As shown in FIG. 10, the thigh phase angle φ defined by the hip joint angle θ and the hip joint angular velocity ω varies between 0 and 2π during a gait cycle.

Specifically, in a case where the hip joint angles θ in a state where the thigh is positioned in front of and behind the user's body axis line along the vertical direction are referred to as "positive" and "negative", respectively, and the hip joint angular velocities ω in a state where the thigh is swung forward and backward are referred to as "positive" and "negative", respectively, when the thigh phase angle φ is 0 in a state where the hip joint angle θ is largest in the "negative" direction and the hip joint angular velocity ω is "zero", the thigh phase angle φ changes from 0 to π/2 during a period (the gait area A1 in FIG. 10) from a state where the thigh is swung backward to the maximum (a state where the hip joint angle θ is largest in the "negative" direction and the hip joint angular velocity ω is "zero", the sampling timing S(1) in FIG. 10) to a state where the thigh moves relatively forward in a swing state and matches the user's body axis line (a state where the hip joint angle θ is "zero" and the hip joint angular velocity ω is largest in the "positive" direction).

Then, the thigh phase angle φ changes from π/2 to π during a period (the gait area A2 in FIG. 10) from a state where the raised thigh in a swing state matches the user's body axis line (a state where the hip joint angle θ is "zero" and the hip joint angular velocity ω is largest in the "positive" direction) to a state where the thigh is further swung relatively forward to the maximum (a state where the hip joint angle θ is largest in the "positive" direction and the hip joint angular velocity ω is "zero").

Then, the thigh phase angle φ changes from the phase angle of π to 3π/2 during a period (the gait area A3 in FIG. 10) from a state where the thigh in a swing state is swung forward to the maximum (a state where the hip joint angle θ is largest in the "positive" direction and the hip joint angular velocity ω is "zero") to a state where the thigh enters a stance state after being in contact with the ground through the heel contact and the thigh in the stance state is swung relatively backward to match the user's body axis line (a state where the hip joint angle θ is "zero" and the hip joint angular velocity ω is largest in the "negative" direction).

Furthermore, the thigh phase angle φ changes from 3π/2 to 2π during a period (the gait area A4 in FIG. 10) from a state where the thigh in the stance state matches the user's body axis line (a state where the hip joint angle θ is "zero" and the hip joint angular velocity ω is largest in the "negative" direction) to a state where the thigh is swung relatively backward and is swung backward to the maximum (a state where the hip joint angle is largest in the "negative" direction and the hip joint angular velocity is "zero").

In the present embodiment, the thigh phase angle calculating unit 550 is configured to perform a latest data transmission process to transmit a thigh phase angle φ(k) calculated based on an angle-related signal at a kth (k is an integer of 1 or more) sampling timing S(k) during a gait cycle as the thigh phase angle at the sampling timing S(k) to the gait motion timing calculating unit 560 and store the thigh phase angle φ(k) as a reference thigh phase angle φc and a stored data transmission process to transmit, instead of the thigh phase angle φ(k) calculated based on the angle-related signal at the kth sampling timing S(k) during the gait cycle, the currently stored reference thigh phase angle φc as the thigh phase angle at the sampling timing S(k) to the gait motion timing calculating unit 560 and continuously store the currently stored reference thigh phase angle φc, performs the stored data transmission process only when conditions are satisfied such that one thigh phase angle calculated based on an angle-related signal at one sampling timing is smaller than the currently stored reference thigh phase angle and an absolute value of a deviation therebetween is equal to or less than a predetermined threshold, and performs the latest data transmission process in other cases.

A detailed description regarding this point will be explained below.

Figure 11:
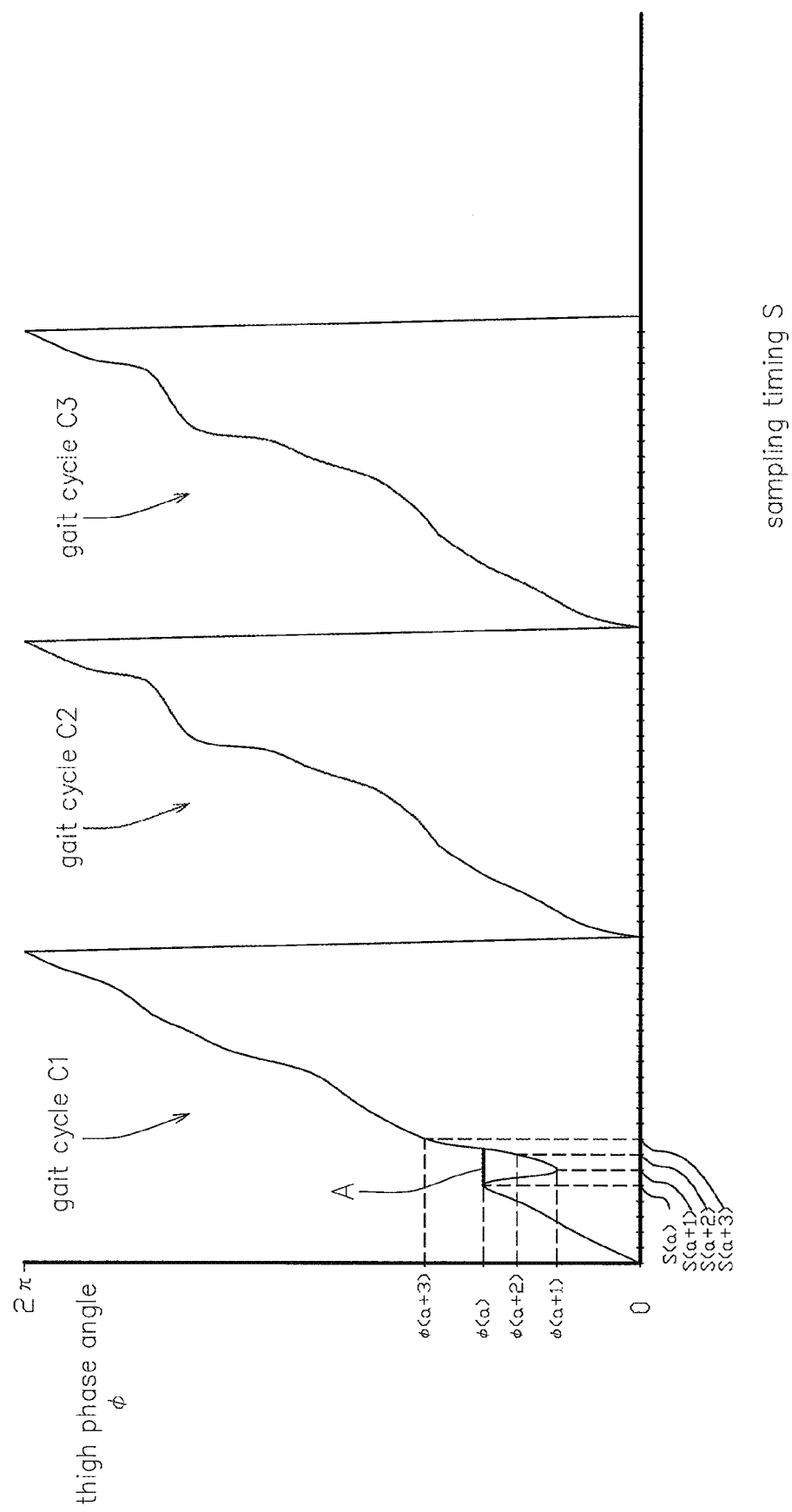
FIG. 11 is a graph showing a relationship between a sampling timing and a thigh phase angle calculated by a thigh phase angle calculating unit.

FIG. 11 is a graph showing a relationship between each sampling timing and the thigh phase angle φ calculated by the thigh phase angle calculating unit 550 at each sampling timing.

In a case where the motion of the thigh during a gait cycle is normal, the thigh phase angle φ calculated by the thigh phase angle calculating unit 550 at each sampling timing gradually increases as the sampling timing S proceeds (that is, with the elapse of time) as shown in gait cycles C2 and C2 in FIG. 11, one gait cycle ends at the time when the thigh phase angle φ reaches 2π, and a subsequent gait cycle starts continuously.

However, for users with leg disability or users with paralysis due to a stroke or the like, there may be a situation where a thigh phase angle φ at one sampling timing is less than the thigh phase angle at the sampling timing immediately before the one sampling timing, i.e., a situation (hereinafter referred to as thigh reverse swing phenomenon) in which the thigh temporarily returns to the side opposite to the direction in which the thigh is supposed to swing during the normal gait motion.

As described above, the gait motion timing calculating unit 560 calculates, based on the thigh phase angle φ sent from the thigh phase angle calculating unit 550, the cycle gait motion timing T that is a percentage relative to the gait cycle. The assisting torque calculating unit 570 calculates, based on the cycle gait motion timing T sent from the gait motion timing calculating unit 560, the torque value that the actuator should output. Then, the operational control unit 580 executes operational control on the actuator so as to output assisting force having the torque value sent from the assisting torque calculating unit 570.

Accordingly, the occurrence of the thigh reverse swing phenomenon results in a situation where the actuator outputs an assisting force having a torque value different from that to be output at the timing, and a vibration may be occurred in some cases.

In the gait cycle C1 in FIG. 11, the thigh phase angle φ calculated by the thigh phase angle calculating unit 550 gradually increases with the elapse of time until sampling timing S(a). In this situation, the thigh phase angle φ calculated based on an angle-related signal, which is sent from the thigh orientation detecting unit 510 at one sampling timing, is larger than the reference thigh phase angle φc currently stored in the thigh phase angle calculating unit 550, and the conditions for performing the stored data transmission process are not satisfied.

Therefore, the thigh phase angle calculating unit 550 performs the latest data transmission process.

On the other hand, the thigh phase angle φ(a+1) calculated by the thigh phase angle calculating unit 550 based on an angle-related signal, which is sent from the thigh orientation detecting unit 510 at a sampling timing S(a+1) in the gait cycle C1 in FIG. 11, is smaller than the currently stored reference thigh phase angle φc (φ(a) in this example) in the thigh phase angle calculating unit 550.

In this case, the thigh phase angle calculating unit 550 performs the stored data transmission process (A part in FIG. 11) to transmit the currently stored reference thigh phase angle φc (φ(a) in this example) as the thigh phase angle φ at the sampling timing S(a+1) to the gait motion timing calculating unit 560.

As described above, the conditions for performing the stored data transmission process includes, in addition to the condition that one thigh phase angle calculated based on an angle-related signal at one sampling timing is smaller than the currently stored reference thigh phase angle, the condition (hereinafter referred to as a second condition of the stored data transmission process) that an absolute value of a deviation between the one thigh phase angle and the currently stored reference thigh phase angle is equal to or less than the predetermined threshold. The second condition of the stored data transmission process will be explained later.

Furthermore, in the gait cycle C1 in FIG. 11, a thigh phase angle φ(a+2) calculated by the thigh phase angle calculating unit 550 based on an angle-related signal, which is sent from the thigh orientation detecting unit 510 at a next sampling timing S(a+2), is also smaller than the currently stored reference thigh phase angle φc (φ(a) in this example) in the thigh phase angle calculating unit 550.

In this case, the thigh phase angle calculating unit 550 performs the stored data transmission process (A part in FIG. 11) to transmit the currently stored reference thigh phase angle φc (φ(a) in this example) as the thigh phase angle φ at the sampling timing S(a+2) to the gait motion timing calculating unit 560.

On the other hand, a thigh phase angle φ(a+3) calculated by the thigh phase angle calculating unit 550 based on an angle-related signal, which is sent from the thigh orientation detecting unit 510 at a sampling timing S(a+3) in the gait cycle C1 in FIG. 11, is larger than the currently stored reference thigh phase angle φc (φ(a) in this example) in the thigh phase angle calculating unit 550, and the conditions for performing the stored data transmission process are not satisfied.

Accordingly, the thigh phase angle calculating unit 550 performs the latest data transmission process to transmit the thigh phase angle φ(a+3) as the thigh phase angle φ at the sampling timing S(a+3) to the gait motion timing calculating unit 560 and store the thigh phase angle φ(a+3) as the reference thigh phase angle φc.

The configuration makes it possible to effectively impart gait assisting force for returning to the normal gait motion even when the thigh reverse swing phenomenon in which the user's thigh swings in a direction opposite to the direction in which it is supposed to swing during the normal gait motion unintentionally occurs during a gait cycle.

Furthermore, the configuration makes it possible to reduce or prevent the output of the actuator from being suddenly changed in an excessive manner due to the unintentional thigh reverse swing phenomenon as much as possible to effectively reduce or prevent the vibration of the actuator.

The second condition of the stored data transmission process will now be explained.

The thigh phase angle φ increases from 0 toward 2π as the sampling timing proceeds (that is, with the elapse of time) in one gait cycle, and the one gait cycle ends at the time when the thigh phase angle φ reaches 2π.

A next sampling timing is a first sampling timing of the subsequent gait cycle, and the thigh phase angle φ again increases from 0 toward 2π as the sampling timing proceeds (that is, with the elapse of time).

In this way, the thigh phase angle φ decreases from 2π to 0 when being changed from one gait cycle to the subsequent gait cycle.

Specifically, at the time when the gait cycle is changed over, in comparison with a thigh phase angle that the thigh phase angle calculating unit 550 calculates based on an angle-related signal at a last sampling timing in one gait cycle, a thigh phase angle that the thigh phase angle calculating unit 550 calculates based on an angle-related signal at a first sampling timing in a subsequent gait cycle substantially decreases by 2π.

Accordingly, setting the predetermined threshold so as to be less than an absolute value (that is, 2π) of a deviation of thigh phase angles when being changed from one gait cycle to the subsequent gait cycle and larger than an absolute value of a deviation of thigh phase angles presumed to be generated due to an unintentional thigh reverse swing phenomenon allows a changeover from one gait cycle to the subsequent gait cycle to be done while allowing the stored data transmission process to be performed to transmit the currently stored reference thigh phase angle φc to the gait motion timing calculating unit 560 when the thigh reverse swing phenomenon occurs.

The predetermined threshold can be arbitrarily set as long as the conditions are satisfied, and can be, for example, 1.8π that is 90% of 2π.

In the present embodiment, the gait motion timing calculating unit 560 has a phase pattern function that converts the thigh phase angle φ into the cycle gait motion timing that is a percentage relative to the gait cycle, and applies the thigh phase angle φ (the thigh phase angle φ(k) that the thigh phase angle calculating unit 550 calculates based on an angle-related signal sent from the thigh orientation detecting unit 510 at the sampling timing S(k), or the reference thigh phase angle φc that the thigh phase angle calculating unit 550 stores at that time when the thigh reverse swing phenomenon occurs) transmitted from the thigh phase angle calculating unit 550 at the sampling timing S(k) to the phase pattern function to calculate a cycle gait motion timing T(k) that corresponds to the sampling timing S(k) during the gait cycle (that is, a percentage of the thigh phase angle φ(k) when a gait cycle is regarded as 100%).

Here, the cycle gait motion timing T(k) is calculated as follows.

$$T(k)=(\varphi(k)/2\pi)\times 100(\%).$$

The assisting torque calculating unit 570 has the output torque pattern defining the relationship between the cycle gait motion timing and the torque value to be output and applies the cycle gait motion timing transmitted from the gait motion timing calculating unit 560 to the output torque pattern to calculate a torque value P(k) to be output for the sampling timing S(k).

The output torque pattern is created for each user and is previously stored in the assisting torque calculating unit 570.

The operational control unit 580 executes operational control on the actuator (the electric motor 130) so as to output the assisting force having the torque value calculated by the assisting torque calculating unit 570.

Thus, the gait motion assisting apparatus 100 according to the present embodiment is configured to determine a gait state (cycle gait motion timing) during a gait cycle based on the phase angle (the thigh phase angle φ) of the thigh different from the lower leg, which is the target part to which the gait assisting force is imparted, and to output the assisting force corresponding to the gait state to the lower leg.

Therefore, compared to the configuration in which the gait state (cycle gait motion timing) is recognized based on the motion of the lower leg, which performs complex motions during gait, the gait state can be recognized accurately, and assisting force suitable for the gait state can be output.

Further, in the gait motion assisting apparatus 100 according to the present embodiment, the thigh phase angle calculating unit 550 calculates the thigh phase angle φ based on the hip joint angle θ and the hip joint angular velocity ω only when the vector length of a plot point on the trajectory diagram defined by the hip joint angle θ and the hip joint angular velocity ω exceeds a predetermined threshold and transmits the thigh phase angle φ to the gait motion timing calculating unit while outputting an actuator operation inhibit signal when the vector length is less than the predetermined threshold.

Thus, it is possible to effectively prevent the actuator (the electric motor 130) from outputting gait assisting force when the user wearing the gait motion assisting apparatus 100 unintentionally changes posture but has not started a gait motion.

Furthermore, as described above, the gait motion assisting apparatus 100 according to the present embodiment is configured to impart gait assisting force to the lower leg by the actuator (the electric motor 130) after recognizing a gait state during a gait cycle based on the thigh phase angle φ.

Therefore, it is possible to provide accurate gait assisting force to a user with hemiplegia due to a stroke, etc.

Specifically, a conventional gait assisting apparatus, which is configured to impart gait assisting force by an actuator such as an electric motor, is configured to detect a motion of a control target part, to which the assisting force is imparted by the actuator, and to execute operational control on the actuator based on the detection result.

For example, it is assumed that a conventional gait assisting apparatus, which feeds gait assisting force to a thigh, executes operational control on an actuator that imparts gait assisting force to the thigh based on a detection result of the motion of the thigh.

Furthermore, it is assumed that a conventional gait assisting apparatus, which feeds gait assisting force to a lower leg, executes operational control on an actuator that imparts gait assisting force to the lower leg based on a detection result of the motion of the lower leg.

However, patients with hemiplegia due to a stroke, or the like, are often not able to perform the normal gait motion of the lower leg (front-back swing motion around the knee joint) although they are able to perform relatively normal gait motion of the thigh (front-back swing motion around the hip joint).

To impart gait assisting force to the lower leg of such a patient, the conventional gait assisting apparatus executes operational control on the actuator that provides gait assisting force to the lower leg based on the motion of the lower leg, which is unable to perform the normal gait motion, which may make it difficult to provide accurate gait assisting force.

Conversely, as described above, the gait motion assisting apparatus 100 according to the present embodiment is configured to execute operational control on the actuator (the electric motor 130) that imparts gait assisting force to the lower leg based on the thigh phase angle φ.

Therefore, even when the user has hemiplegia due to a stroke or the like, it is possible to provide accurate gait assisting force to the lower leg.

In a preferable configuration, the thigh phase angle calculating unit 550 may be configured to calculate the thigh phase angle φ(k) by using a normalized hip joint angle θa(k) and a normalized hip joint angular velocity ωa(k) instead of the hip joint angle θ(k) (hereinafter also referred to as the unnormalized hip joint angle θ(k) as appropriate) calculated based on an angle-related signal from the thigh orientation detecting unit 510 and the hip joint angular velocity ω(k) (hereinafter also referred to as the unnormalized hip joint angular velocity ω(k) as appropriate) obtained by differentiating the unnormalized hip joint angle θ(k).

That is, the thigh phase angle calculating unit 550 may be configured to divide the unnormalized hip joint angle θ(k) by a stored hip joint angle normalization coefficient A to calculate the normalized hip joint angle θa(k), divide the unnormalized hip joint angular velocity ω(k) by a stored hip joint angular velocity normalization coefficient B to calculate the normalized hip joint angular velocity ωa(k), and calculate the thigh phase angle φ(k) (=−Arctan(ωa(k)/θa(k))+π) by using the normalized hip joint angle θa(k) and the normalized hip joint angular velocity ωa(k).

With this configuration, it is possible to accurately recognize a gait state (cycle gait motion timing) during a gait cycle.

Specifically, FIG. 10 schematically illustrates the trajectory diagram of the thigh phase angle φ in a state where the scale (amplitude) of the hip joint angle θ matches the scale (amplitude) of the hip joint angular velocity ω for easier understanding; however, in reality, the scale (amplitude) of the hip joint angle θ does not match the scale (amplitude) of the hip joint angular velocity ω, and they are different from user to user, more strictly speaking, may differ from gait cycle to gait cycle even for the same user.

Figure 12:
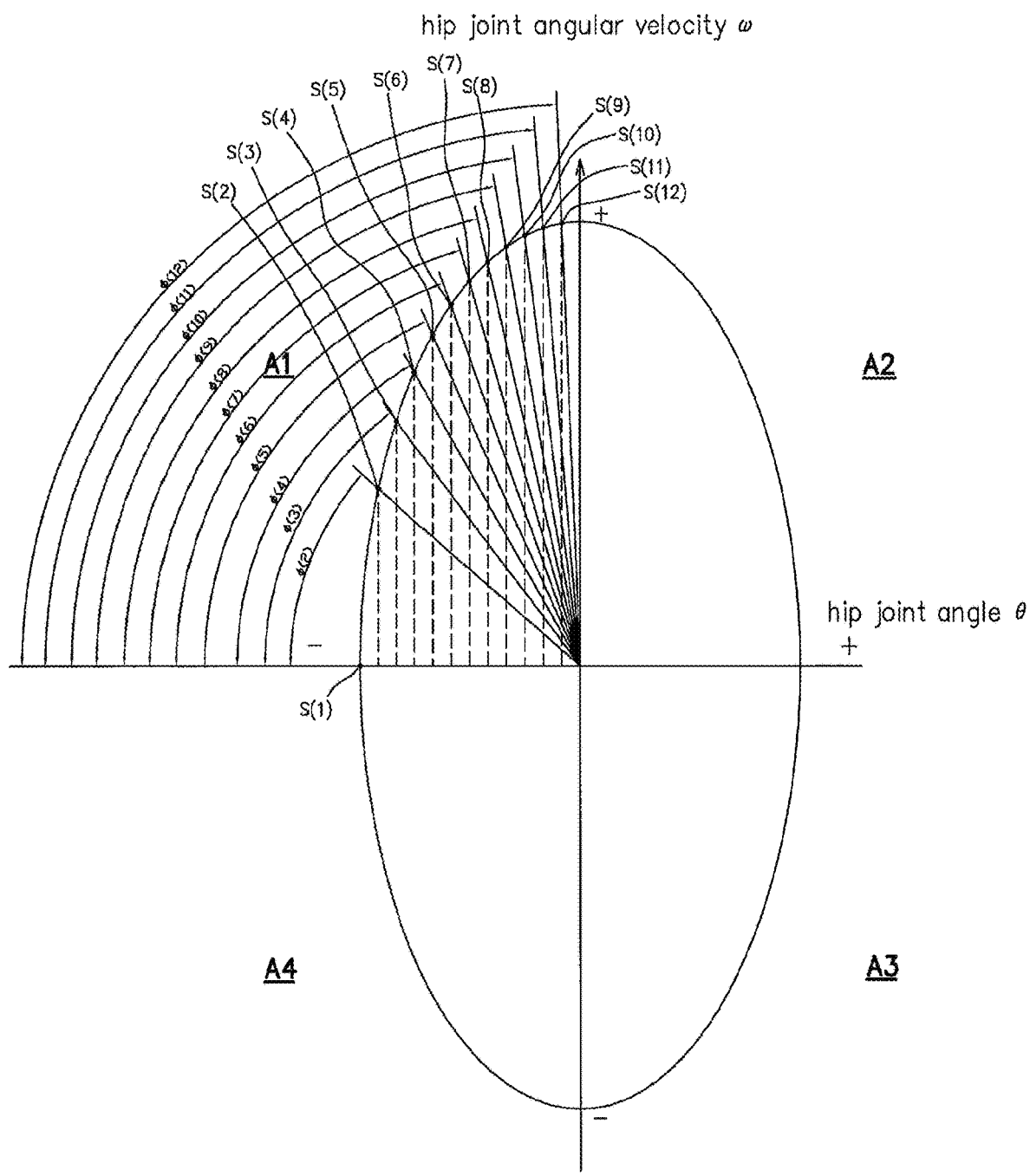
FIG. 12 is a trajectory diagram obtained by plotting hip joint angles θ and hip joint angular velocities ω over a gait cycle in a state where the scale (amplitude) of the hip joint angular velocity ω is approximately twice the scale (amplitude) of the hip joint angle θ, the angles θ and the velocities ω being calculated by the control device of the gait motion assisting apparatus.

FIG. 12 shows a schematic diagram of a trajectory diagram during a gait cycle of a user.

In the example shown in FIG. 12, the scale (amplitude) of the hip joint angular velocity ω is approximately twice the scale (amplitude) of the hip joint angle θ.

Furthermore, S(1) in FIG. 10 and FIG. 12 is a sampling timing when the hip joint angle θ is largest in the "negative" direction and the hip joint angular velocity ω is "zero", and the sampling timings S(2) to S(12) are sampling timings that follow the sampling timing S(1).

Further, thigh phase angles φ(2) to φ(12) are thigh phase angles obtained based on measurement values at the sampling timings S(2) to S(12), respectively.

As is clear from the comparison between FIG. 10 and FIG. 12, in FIG. 12, compared to FIG. 10, the rate of change in the thigh phase angle φ with respect to an elapsed time (i.e., the deviation of the thigh phase angle φ between one sampling timing and the subsequent sampling timing) is large in a region (e.g., the sampling timings S(1) to S(3)) where the absolute value of the hip joint angle θ is large, while the rate of change in the thigh phase angle φ with respect to an elapsed time is small in a region (e.g., the sampling timing S(7) to the sampling timing S(12)) where the absolute value of the hip joint angle θ is small.

As described above, the thigh phase angle φ(k) at the sampling timing S(k) is represented by the cycle gait motion timing T(k) that is defined using a percentage relative to the gait cycle as follows.

$$T(k)=(\varphi(k)/2\pi)\times 100(\%)$$

Therefore, when the scale (amplitude) of the hip joint angle θ is different from the scale (amplitude) of the hip joint angular velocity ω, the rate of change in the cycle gait motion timing calculated based on the thigh phase angle φ largely changes depending on the swing position of the thigh (i.e., the magnitude of the absolute value of the hip joint angle θ) during a gait cycle, which accordingly makes it difficult to properly recognize the cycle gait motion timing and makes it difficult to accurately obtain the torque value to be output by the actuator.

In consideration of this point, the unnormalized hip joint angle θ(k) may be divided by the hip joint angle normalization coefficient A to calculate the normalized hip joint angle θa(k), the unnormalized hip joint angular velocity ω(k) obtained by differentiating the unnormalized hip joint angle θ(k) may be divided by the hip joint angular velocity normalization coefficient B to calculate the normalized hip joint angular velocity ωa(k), and the thigh phase angle φ(k) (=−Arctan(ωa(k)/θa(k))+π) may be calculated by using the normalized hip joint angle θa(k) and the normalized hip joint angular velocity ωa(k).

With this configuration, the difference in the scale (amplitude) between the hip joint angle θa(k) and the hip joint angular velocity ωa(k), based on which the thigh phase angle φ(k) is calculated, can be prevented or reduced, and the cycle gait motion timing can be recognized accurately over a gait cycle.

For example, the thigh phase angle calculating unit 550 may be configured to store the maximum absolute value among the unnormalized hip joint angles θ obtained based on the angle-related signals from the thigh orientation detecting unit 510 within a predetermined time period as the hip joint angle normalization coefficient A and store the maximum absolute value among the unnormalized hip joint angular velocities ω calculated by differentiating the unnormalized hip joint angles θ obtained during the predetermined time period as the hip joint angular velocity normalization coefficient B.

With this configuration, the hip joint angle normalization coefficient A and the hip joint angular velocity normalization coefficient B corresponding to a different gait "habit" of each user can be obtained, and the recognition accuracy of the cycle gait motion timing can be improved.

Alternatively, a modification may be made such that the thigh phase angle calculating unit 550 stores a human-input hip joint angle and a human-input hip joint angular velocity, which are previously input, as the hip joint angle normalization coefficient A and the hip joint angular velocity normalization coefficient B, respectively.

In this modification, the human-input hip joint angle and the human-input hip joint angular velocity can be set for each user based on the user's past gait data.

In the above-described modification, preferably, the thigh phase angle calculating unit 550 may be configured to save the maximum absolute value among the unnormalized hip joint angles θ obtained based on the angle-related signals from the thigh orientation detecting unit 510 within a predetermined time period as the hip joint angle normalization coefficient A instead of the human-input hip joint angle and save the maximum absolute value among the unnormalized hip joint angular velocities ω calculated by differentiating the unnormalized hip joint angles θ obtained during the predetermined time period as the hip joint angular velocity normalization coefficient B instead of the human-input hip joint angular velocity.

The predetermined time period can be, for example, a predetermined number of most recently completed gait cycles or a time period from when the main power of the gait motion assisting apparatus 100 is turned on to the most recently completed gait cycle.

The predetermined number can be set appropriately to an integer of 1 or more.

Next, the gait assisting force required for a gait motion is described.

Figure 13:
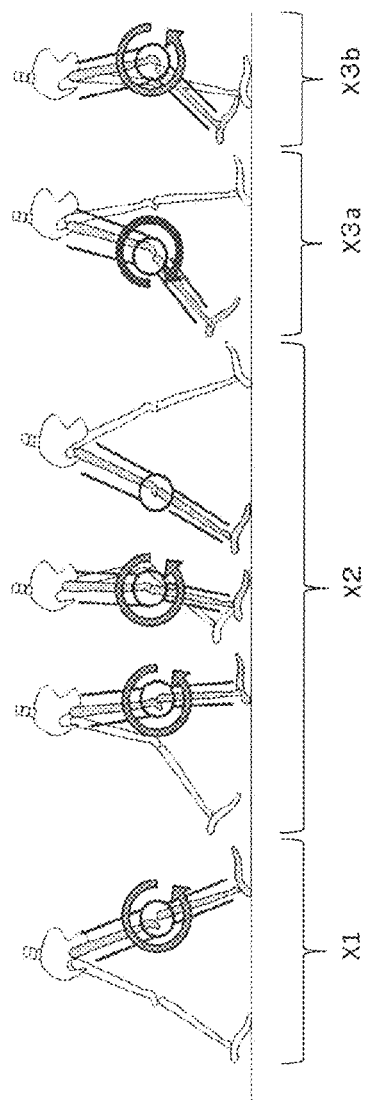
FIG. 13 is a schematic diagram showing gait posture during a gait cycle over time.

FIG. 13 is a schematic diagram showing gait posture during a gait cycle over time.

As shown in FIG. 13, a gait cycle includes a heel contact phase (a period before and after the forward-raised foot contacts the floor) X1 including a heel contact time point when the heel contacts the ground in front of the user's body axis line (vertical axis line), a stance phase (a period when the floor-contacted lower leg is moved relatively backward relative to the body) X2 when the heel-contacted leg after heel contact is moved relatively backward while being in contact with the ground, an initial stage X3a of a swing phase when the lower leg of the leg contacting the ground is raised after the stance phase X2, and a later stage X3b of the swing phase when the raised lower leg is moved relatively forward and led to heel contact.

Gait assisting force includes force for pushing the lower leg in the extending direction relative to the thigh and force for pushing the lower leg in the bending direction relative to the thigh, and the direction of necessary gait assisting force varies according to a motion timing during a gait cycle.

For example, in the heel contact phase X1 and the stance phase X2, extending-direction gait assisting force for rotating the lower leg in the knee extending direction around the knee joint to prevent knee bending is necessary.

In the initial stage X3a of the swing phase, bending-direction gait assisting force for assisting the raising of the leg by rotating the lower leg around the knee joint in the knee bending direction is necessary.

In the later stage X3b of the swing phase, gait assisting force for rotating the lower leg around the knee joint in the knee extending direction is necessary.

In addition, the necessity of gait assisting force in any or all of the four stages and/or the degree of gait assisting force necessary in a desired stage varies for each user and/or according to the degree of recovery of the user.

In consideration of this point, the output torque pattern is set for each user and in accordance with each degree of user's recovery.

Figure 14:
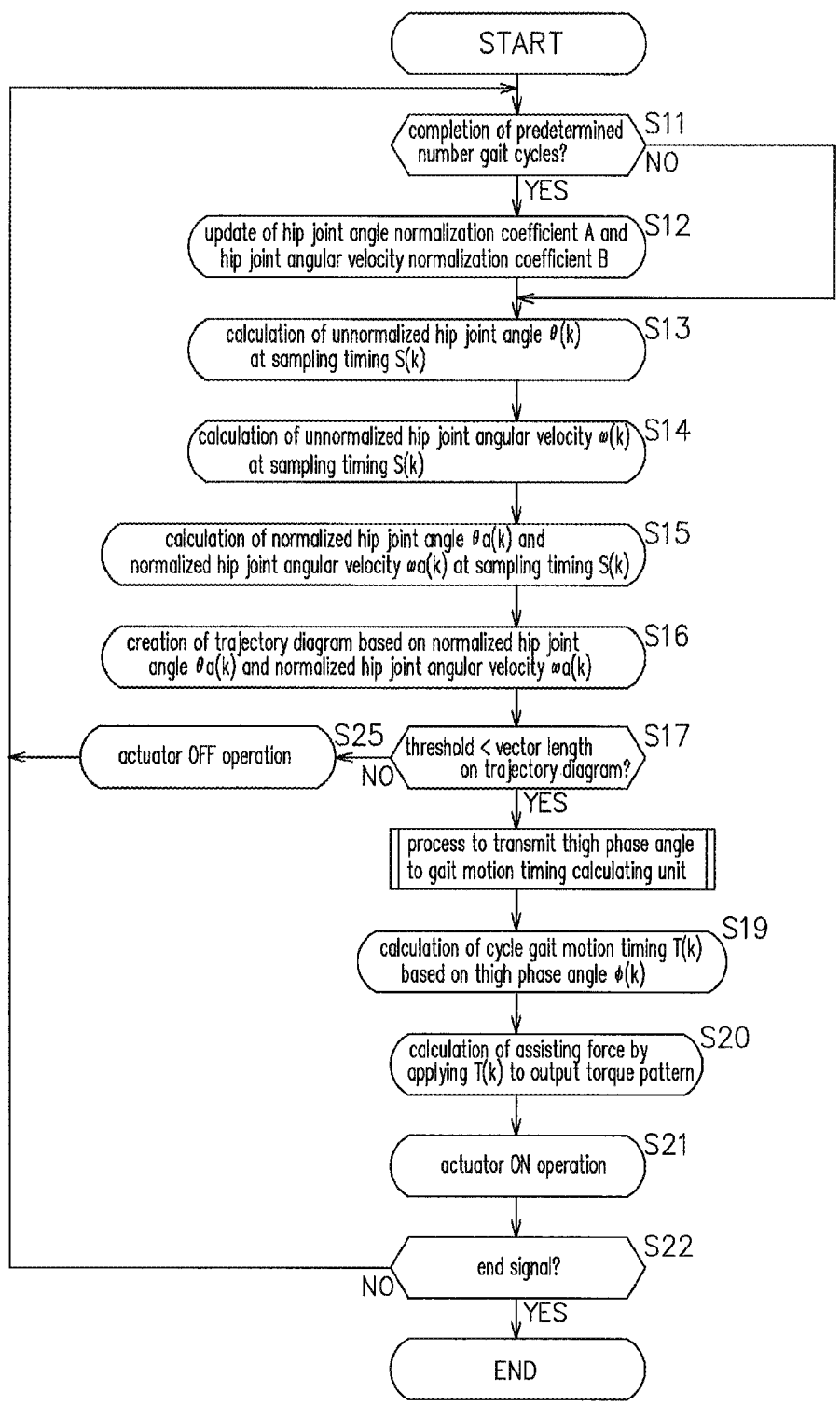
FIG. 14 is a flow diagram of an actuator operational control mode executed by the control device of the gait motion assisting apparatus.

FIG. 14 shows a flow of an actuator operational control mode by the control device 500 in the gait motion assisting apparatus 100.

In response to an activation signal input, the control device 500 activates the actuator operational control mode.

The activation signal is input in response to, for example, a human operation by the user to a human-operated member such as a start button.

When the actuator operational control mode is activated, the thigh phase angle calculating unit 550 determines, at Step S11, whether a predetermined number of gait cycles has been completed.

It may be determined whether the predetermined number of gait cycles has been completed by counting the number of times the thigh phase angle φ(k) calculated in "process to transmit the thigh phase angle to the gait motion timing calculating unit", which is describe below, is returned to a preset gait cycle reference angle (for example, 0) and determining whether this count reaches the predetermined number.

In the case of YES at Step S11, the process proceeds to Step S12, and in the case of NO at Step S11, the process bypasses Step S12 and proceeds to Step S13.

Immediately after the activation of the actuator operational control mode, a NO determination is made at Step S11 and the process proceeds to Step S13.

Furthermore, Step S12 will be described below.

At Step S13, the thigh phase angle calculating unit 550 calculates the unnormalized hip joint angle θ(k) at a sampling timing S(k) from the thigh orientation detecting unit 510 based on the angle-related signal at the sampling timing S(k) and, at Step S14, calculates the unnormalized hip joint angular velocity ω(k) at the sampling timing S(k) based on the unnormalized hip joint angle θ(k).

At Step S15, the thigh phase angle calculating unit 550 divides the unnormalized hip joint angle θ(k) by the stored hip joint angle normalization coefficient A to calculate the normalized hip joint angle θa(k) at the sampling timing S(k) and divides the unnormalized hip joint angular velocity by the stored hip joint angular velocity normalization coefficient B to calculate the normalized hip joint angular velocity ωa(k) at the sampling timing S(k).

The thigh phase angle calculating unit 550 creates a trajectory diagram based on the normalized hip joint angle θa(k) and the normalized hip joint angular velocity ωa(k) at Step 16 and determines whether the vector length of the plot point (the distance between the plot point and the origin) on the trajectory diagram exceeds a threshold at Step S17.

In the case of NO at Step S17 described above, the thigh phase angle calculating unit 550 determines that no gait motion has been started and outputs an actuator operation inhibit signal (Step S25).

In this case, the actuator operational control mode returns to Step S11.

In the case of YES at Step S17 described above, a "process to transmit the thigh phase angle to the gait motion timing calculating unit" is executed.

Figure 15:
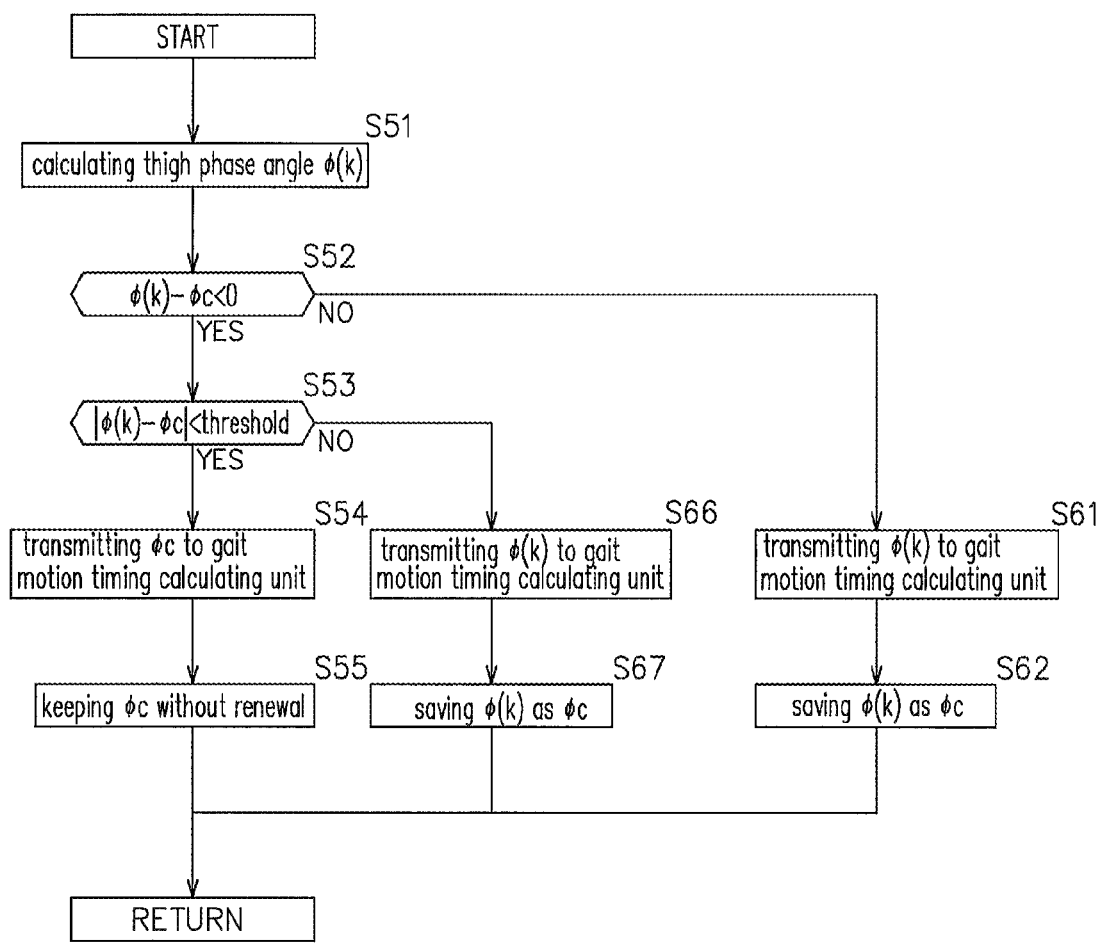
FIG. 15 is a flow diagram of "process to transmit the thigh phase angle to the gait motion timing calculating unit" in the actuator operational control mode.

FIG. 15 shows the flow of the "process to transmit the thigh phase angle to the gait motion timing calculating unit".

The thigh phase angle calculating unit 550 calculates the thigh phase angle φ(k) based on the hip joint angle θ(k) and the hip joint angular velocity ω(k) at the sampling timing S(k) (in the present embodiment, the normalized hip joint angle θa(k) and the normalized hip joint angular velocity ωa(k)) (Step S51).

Subsequently, the thigh phase angle calculating unit 550 determines whether the thigh phase angle φ(k) is smaller than the currently stored reference thigh phase angle φc (Step S52).

Here, the default value of the reference thigh phase angle φc is 0 and, if the reference thigh phase angle φc is saved at Steps S55, S62, and S67 described below, is the stored value.

In the case of NO at Step S52, that is, when the thigh phase angle φ(k) calculated at Step S51 is larger than the reference thigh phase angle φc, it unit that the normal gait motion (i.e., a gait motion in which the thigh phase angle φ increases with the elapse of time) is being performed.

In this case, the thigh phase angle calculating unit 550 transmits the thigh phase angle φ(k) calculated based on the angle-related signal at the sampling timing S(k) as the thigh phase angle φ at the sampling timing S(k) to the gait motion timing calculating unit 560 (Step S61), saves the thigh phase angle φ(k) as the new reference thigh phase angle φc (Step S62), and ends the "process to transmit the thigh phase angle to the gait motion timing calculating unit".

Accordingly, in this case, at Step S52 of the "process to transmit the thigh phase angle to the gait motion timing calculating unit" for the subsequent sampling timing S(k+1), it is determined whether the thigh phase angle φ(k+1) calculated based on the angle-related signal at the sampling timing S(k+1) is smaller than the thigh phase angle φ(k) stored as the reference thigh phase angle φc.

In the case of YES at Step S52 described above, that is, when the thigh phase angle φ(k) calculated at Step S51 is smaller than the reference thigh phase angle φc, it unit that the normal gait motion (i.e., a gait motion in which the thigh phase angle increases with the elapse of time) is not being performed and there is a possibility of occurrence of the above-described thigh reverse swing phenomenon.

In this case, the thigh phase angle calculating unit 550 determines whether the absolute value of the deviation between the thigh phase angle φ(k) and the reference thigh phase angle φc is smaller than a predetermined threshold (Step S53).

Step S53 is a step for determining whether the situation where the thigh phase angle φ(k) calculated at Step S51 is smaller than the reference thigh phase angle φc is caused by an unintended thigh reverse swing phenomenon or by gait cycle switching from one gait cycle to the subsequent gait cycle.

As described above, the predetermined threshold at Step S53 is set such that a NO determination is made at Step S53 when the gait cycle is switched.

The predetermined threshold is, for example, 90% (1.8π) of the change range (2π) of the thigh phase angle over the entire gait cycle.

In the case of NO at Step S53, the thigh phase angle calculating unit 550 determines that the situation where the calculated thigh phase angle φ(k) is smaller than the reference thigh phase angle φc is caused by gait cycle switching from one gait cycle to the subsequent gait cycle, transmits the thigh phase angle φ(k) calculated based on the angle-related signal at the sampling timing S(k) as the thigh phase angle at the sampling timing S(k) to the gait motion timing calculating unit 560 (Step S66), stores the thigh phase angle φ(k) as the new reference thigh phase angle φc (Step S67), and ends the above-described "process to transmit the thigh phase angle to the gait motion timing calculating unit".

Therefore, in this case, at Step S52 of the "process to transmit the thigh phase angle to the gait motion timing calculating unit" for the subsequent sampling timing S(k+1), it is determined whether the thigh phase angle φ(k+1) calculated based on the angle-related signal at the sampling timing S(k+1) is lower than the thigh phase angle φ(k) stored as the reference thigh phase angle φc.

In the case of YES at Step S53, the thigh phase angle calculating unit 550 determines that an unintended thigh reverse swing phenomenon is occurring and transmits the reference thigh phase angle φc instead of the thigh phase angle φ(k) calculated based on the angle-related signal at the sampling timing S(k) to the gait motion timing calculating unit 560 (Step S54).

In this case, the thigh phase angle calculating unit 550 stores the currently stored reference thigh phase angle φc without change (Step S55) and ends the above-described "process to transmit the thigh phase angle to the gait motion timing calculating unit".

Accordingly, in this case, at Step S52 of the "process to transmit the thigh phase angle to the gait motion timing calculating unit" at the subsequent sampling timing S(k+1), it is determined whether the thigh phase angle φ(k+1) calculated based on the angle-related signal at the sampling timing S(k+1) is lower than the continuously stored reference thigh phase angle φc.

When the "process to transmit the thigh phase angle to the gait motion timing calculating unit" has ended, the gait motion timing calculating unit 560 calculates the cycle gait motion timing T(k) based on the thigh phase angle (the thigh phase angle φ(k) or the reference thigh phase angle φc) transmitted from the thigh phase angle calculating unit 550 and transmits it to the assisting torque calculating unit 570 (Step S19), as shown in FIG. 14.

The assisting torque calculating unit 570 applies the cycle gait motion timing T(k) from the gait motion timing calculating unit 560 to the stored output torque pattern, acquires the magnitude and direction of the gait assisting force to be output by the actuator at this timing (the sampling timing S(k)), and transmits them to the operational control unit 580 (Step S20).

The operational control unit 580 executes operational control on the actuator so as to output the gait assisting force having the magnitude and direction calculated by the assisting torque calculating unit 570 (Step S21).

At Step S22, the control device 500 determines whether an end signal for the actuator operational control mode has been input, returns to Step S11 when no end signal has been input, and ends the control mode when an end signal has been input.

Furthermore, for example, the end signal is input in response to a human operation by the user to a human-operated member such as an end button.

When the process returns from Step S22 to Step S11, the thigh phase angle calculating unit 550 determines whether the number of gait cycles counted at Step S11 described above has reached the predetermined number, and if YES, proceeds to Step S12.

At Step S12, the thigh phase angle calculating unit 550 saves the maximum absolute value among the unnormalized hip joint angles θ obtained based on the angle signals from the thigh orientation detecting unit 510 within the predetermined number of gait cycles as the hip joint angle normalization coefficient A and saves the maximum absolute value among the unnormalized hip joint angular velocities ω calculated by differentiating the unnormalized hip joint angles θ obtained based on the angle signals from the thigh orientation detecting unit 510 within the predetermined number of gait cycles as the hip joint angular velocity normalization coefficient B.

Furthermore, in the present embodiment, as described above, a configuration is made to determine the occurrence of a thigh reverse swing phenomenon based on the thigh phase angle; however, alternatively a configuration may be made to determine the occurrence of a thigh reverse swing phenomenon based on the cycle gait motion timing.

Specifically, the gait motion timing calculating unit 560 may be configured to have a latest data transmission process to transmit the cycle gait motion timing T(k) calculated based on the angle-related signal at a kth sampling timing S(k) (k is an integer of 1 or more) during a gait cycle as the cycle gait motion timing at the sampling timing S(k) to the assisting torque calculating unit 570 and store the cycle gait motion timing T(k) as the reference cycle gait motion timing Tc and a stored data transmission process to transmit, instead of the cycle gait motion timing T(k) calculated based on the angle-related signal at the kth sampling timing S(k) during a gait cycle, the currently stored reference cycle gait motion timing Tc as the cycle gait motion timing at the sampling timing S(k) to the assisting torque calculating unit 570 and continuously store the currently stored reference cycle gait motion timing Tc, perform the stored data transmission process only when conditions are satisfied such that one cycle gait motion timing calculated based on an angle-related signal at one sampling timing is smaller than the currently stored reference cycle gait motion timing and the absolute value of the deviation is less than a predetermined threshold, and perform the latest data transmission process in other cases.

With this configuration, too, as in the present embodiment, gait assisting force can be imparted as smoothly as possible even in the case of occurrence of an unintended thigh reverse swing phenomenon.

Further, in this case, the predetermined threshold can be, for example, 90% in a case where the cycle gait motion timing during a gait cycle is 0 to 100%.

The invention claimed is:

1. A gait motion assisting apparatus comprising:
    an actuator that imparts assisting force to a user's gait motion;
    a thigh orientation detecting unit that detects an angle-related signal that is related to a hip joint angle, which is a front-back swing angle of the user's thigh, at each sampling timing;
    a thigh phase angle calculating unit that calculates a thigh phase angle at each sampling timing based on the angle-related signal;
    a gait motion timing calculating unit that calculates a cycle gait motion timing that is a percentage relative to a gait cycle based on the thigh phase angle from the thigh phase angle calculating unit;
    an assisting torque calculating unit that has an output torque pattern defining a relationship between the cycle gait motion timing and a torque value to be outputted and applies the cycle gait motion timing transmitted from the gait motion timing calculating unit to the output torque pattern to calculate the torque value corresponding to the sampling timing; and
    an operational control unit that executes operational control on the actuator so as to output assisting force having the torque value calculated by the assisting torque calculating unit,
    wherein the thigh phase angle calculating unit has a latest data transmission process to transmit a thigh phase angle φ(k) calculated based on an angle-related signal at a kth (k is an integer of 1 or more) sampling timing S(k) during the gait cycle as the thigh phase angle at the sampling timing S(k) to the gait motion timing calculating unit and store the thigh phase angle φ(k) as a reference thigh phase angle φc and a stored data transmission process to transmit, instead of the thigh phase angle φ(k) calculated based on the angle-related signal at the kth sampling timing S(k) during the gait cycle, the currently stored reference thigh phase angle φc as the thigh phase angle at the sampling timing S(k) to the gait motion timing calculating unit and continuously store the currently stored reference thigh phase angle φc, and is configured to perform the stored data transmission process only when conditions are satisfied such that the thigh phase angle calculated based on the angle-related signal at the kth sampling timing is smaller than the currently stored reference thigh phase angle and an absolute value of a deviation therebetween is equal to or less than a predetermined threshold, and performs the latest data transmission process in other cases.

2. The gait motion assisting apparatus according to claim 1, wherein the predetermined threshold is 1.87π.

3. The gait motion assisting apparatus according to claim 1, wherein the gait motion timing calculating unit has a conversion function specifying a relationship between the thigh phase angle and the cycle gait motion timing during the gait cycle and applies the thigh phase angle transmitted from the thigh phase angle calculating unit to the conversion function to calculate the cycle gait motion timing.

4. A gait motion assisting apparatus comprising:
    an actuator that imparts assisting force to a user's gait motion;
    a thigh orientation detecting unit that detects an angle-related signal that is related to a hip joint angle, which is a front-back swing angle of the user's thigh, at each sampling timing;
    a thigh phase angle calculating unit that calculates a thigh phase angle at each sampling timing based on the angle-related signal;
    a gait motion timing calculating unit that calculates a cycle gait motion timing that is a percentage relative to a gait cycle based on the thigh phase angle from the thigh phase angle calculating unit;
    an assisting torque calculating unit that has an output torque pattern defining a relationship between the cycle gait motion timing and a torque value to be outputted and applies the cycle gait motion timing transmitted from the gait motion timing calculating unit to the output torque pattern to calculate the torque value corresponding to the sampling timing; and
    an operational control unit that executes operational control on the actuator so as to output assisting force having the torque value calculated by the assisting torque calculating unit,
    wherein the gait motion timing calculating unit has a latest data transmission process to transmit a cycle gait motion timing T(k) calculated based on an angle-related signal at a kth sampling timing S(k) (k is an integer of 1 or more) during the gait cycle as the cycle gait motion timing at the sampling timing S(k) to the assisting torque calculating unit and store the cycle gait motion timing T(k) as a reference cycle gait motion timing Tc and a stored data transmission process to transmit, instead of the cycle gait motion timing T(k) calculated based on the angle-related signal at the kth sampling timing S(k) during the gait cycle, the currently stored reference cycle gait motion timing Tc as the cycle gait motion timing at the sampling timing S(k) to the assisting torque calculating unit and continuously store the currently stored reference cycle gait motion timing Tc, and is configured to perform the stored data transmission process only when conditions are satisfied such that the cycle gait motion timing calculated based on the angle-related signal at the sampling timing is smaller than the currently stored reference cycle gait motion timing and an absolute value of a deviation therebetween is equal to or less than a predetermined threshold, and performs the latest data transmission process in other cases.

5. The gait motion assisting apparatus according to claim 4, wherein the predetermined threshold is 90% when the cycle gait motion timing during the gait cycle is 0 to 100%.

* * * * *